US007276241B2

(12) United States Patent
Schneider et al.

(10) Patent No.: US 7,276,241 B2
(45) Date of Patent: Oct. 2, 2007

(54) METHODS OF TREATING A TUMOR THAT EXPRESSES APRIL BY ADMINISTERING BCMA

(75) Inventors: Pascal Schneider, Epalinges (CH); Jeffrey Thompson, Stoneham, MA (US); Teresa Cachero, Brookline, MA (US); Christine Ambrose, Reading, MA (US); Paul Rennert, Millis, MA (US)

(73) Assignees: Biogen Idec MA Inc., Cambridge, MA (US); Apoxis SA, Epalinges (CH)

( * ) Notice: Subject to any disclaimer, the term of this patent is extended or adjusted under 35 U.S.C. 154(b) by 549 days.

(21) Appl. No.: 10/115,192

(22) Filed: Apr. 2, 2002

(65) Prior Publication Data

US 2003/0082175 A1    May 1, 2003

Related U.S. Application Data

(63) Continuation of application No. PCT/US00/27579, filed on Oct. 5, 2000.

(60) Provisional application No. 60/215,688, filed on Jun. 30, 2000, provisional application No. 60/181,807, filed on Feb. 11, 2000, provisional application No. 60/157,933, filed on Oct. 6, 1999.

(51) Int. Cl.
    *A61K 39/00*    (2006.01)
    *A61K 38/00*    (2006.01)
(52) U.S. Cl. ............................ 424/185.1; 424/192.1; 514/12
(58) Field of Classification Search ............ None
    See application file for complete search history.

(56) References Cited

U.S. PATENT DOCUMENTS

| 5,969,102 A | 10/1999 | Bram et al. ............ 530/350 |
| 6,297,367 B1 | 10/2001 | Tribouley ............ 536/23.5 |
| 6,316,222 B1 | 11/2001 | Bram et al. ............ 435/69.1 |
| 6,475,986 B1 | 11/2002 | Aggarwal ............ 514/12 |
| 6,475,987 B1 | 11/2002 | Shu |
| 6,541,224 B2 | 4/2003 | Yu et al. ............ 435/69.5 |
| 6,774,106 B2 | 8/2004 | Theill et al. |
| 2002/0037852 A1 | 3/2002 | Browning et al. |
| 2002/0086018 A1 | 7/2002 | Theill et al. |
| 2002/0165156 A1 | 11/2002 | Browning et al. |
| 2002/0172674 A1 | 11/2002 | Browning et al. |
| 2003/0023038 A1 | 1/2003 | Rennert et al. |
| 2004/0013674 A1 | 1/2004 | Ambrose et al. |
| 2004/0072188 A1 | 4/2004 | Ambrose et al. |
| 2006/0067933 A1 | 3/2006 | Gross et al. |

FOREIGN PATENT DOCUMENTS

| EP | 0 869 180 A1 | 10/1998 |
| WO | WO97/33902 | 9/1997 |
| WO | WO98/18921 | 5/1998 |
| WO | WO98/27114 | 6/1998 |
| WO | WO98/55620 | 12/1998 |
| WO | WO98/55621 | 12/1998 |
| WO | WO99/11791 | 3/1999 |
| WO | WO99/12964 | 3/1999 |
| WO | WO99/12965 | 3/1999 |
| WO | WO99/33980 | 7/1999 |
| WO | WO 00/26244 | 5/2000 |
| WO | WO 00/39295 | 7/2000 |
| WO | WO 00/40716 | 7/2000 |
| WO | WO 00/43032 | 7/2000 |
| WO | WO 00/50597 | 8/2000 |
| WO | WO 00/50633 | 8/2000 |
| WO | WO 00/58362 | 10/2000 |
| WO | WO 00/68378 | 11/2000 |
| WO | WO 01/12812 | 2/2001 |
| WO | WO 01/087977 | 11/2001 |
| WO | WO 01/087979 | 11/2001 |
| WO | WO 02/02641 | 1/2002 |
| WO | WO 02/18620 | 3/2002 |
| WO | WO 03/055979 | 7/2003 |

OTHER PUBLICATIONS

Ngo et al., 1994, The Protein Folding Problem and Tertiary Structure Prediction, pp. 492-495.*
Wells, Aditivity of Mutational Effects in Proteins, 1990, Biochemistry, vol. 26, No. 37, pp. 8509-8517.*
Hane et al. (1998), APRIL, a New Ligand of the Tumor Necrosis Factor Family, Stimulates Tumor Cell Growth, J. Exp. Med. vol. 11, No. 6, pp. 1185-1190.*
Bork, A. Powers and pitfalls in sequence aalysis: the 70% hurdle, (2000), Genome Res. 10: pp. 398-400.*
Skolnick et al. From genes to protein structure and function: novel applications of computational approches in the genomic era, (2000), Trends in Biotech. 18(1): pp. 34-39.*
Doerks et al. Protein annotation: detective work for function prediction, (1998), Trends in Genetics. 14(6): pp. 248-250.*
Smith et al. the challenges of genome sequence annotation or "The devil is in the details", (1997), Nature Biotech 15: pp. 1222-1223.*
Brenner, S.E. Errors in genome function (1999), Trends in Genetics 15(40: pp. 132-133.*
Bork et al. go hunting in sequence databases but watch out for traps (1996), Trends in Genetics 12(10): pp. 425-427.*
Gras et al., "BCMAp: An Integral Membrane Protein in the Golgi Apparatus of Human Mature B Lymphocytes", International Immunology, vol. 7, No. 7, 1995, pp. 1093-1106.
Gross et al., "TACI and BCMA are Receptors for a TNF Homologue Implicated in B-Cell Autoimmune Disease", Nature, vol. 404, Apr. 27, 2000, pp. 995-999.
Hahne et al., "APRIL, A New Ligand of the Tumor Necrosis Factor Family. Stimulates Tumor Cell Growth", J. Exp. Med., vol. 188. No. 6, Sep. 21, 1998, pp. 1185-1190.

(Continued)

*Primary Examiner*—Christine J. Saoud
*Assistant Examiner*—Jegatheesan Seharaseyon
(74) *Attorney, Agent, or Firm*—Finnegan, Henderson, Farabow, Garrett & Dunner, LLP

(57) ABSTRACT

A novel receptor in the TNF family is provided: APRIL-R. Chimeric molecules and antibodies to APRIL-R and methods of use thereof are also provided.

24 Claims, 33 Drawing Sheets

OTHER PUBLICATIONS

Khare et al., "Severe B Cell Hyperplasia and Autoimmune Disease in TALL-1 Transgenic Mice", Proceedings of the National Academy of Sciences of the United States of America. Mar. 28, 2000, vol. 97, No. 7, pp. 3370-3375.

Kwon et al.. "Functions of Newly Identified Members of the Tumor Necrosis Factor Receptor/Ligand Superfamilies in Lymphocytes", Current Opinion in Immunology. 1999, pp. 340-345.

Laabi et al., "A New Gene, BCM, on Chromosome 16 is Fused to the Interleukin 2 Gene by a t(4:16) (q26:p13) Translocation in a Malignant T Cell Lymphoma", The EMBO Journal, vol. 11. No. 11, 1992, pp. 3897-3904.

Laabi et al., "The BCMA Gene, Preferentially Expressed During B Lymphoid Maturation, is Bidirectionally Transcribed", Nucleic Acids Research, vol. 22, No. 7, 1994, pp. 1147-1154.

Mackay et al., "Mice Transgenic for BAFF Develop Lymphocytic Disorders along with Autoimmune Manifestations", Journal of Experimental Medicine, Dec. 6, 1999, vol. 190, No. 11, pp. 1697-1710.

Maldry et al., "The Characterization of Murine BCMA Gene Defines it as a New Memer of the Tumor Necrosis Factor Receptor Superfamily", International Immunology, vol. 10, No. 11, 1998, pp. 1693-1702.

Mukhopadhyay et al., "Identification and Characterization of a Novel Cytokine, THANK, a TNF Homologue that Activates Apoptosis, Nuclear Factor-kappaB, and c-Jun NH2-Terminal Kinase", Journal of Biological Chemistry, Jun. 4, 1999, vol. 274, No. 23, pp. 15978-15981.

Moore et al., "BLyS: Member of the Tumor Necrosis Factor Family and B Lymphocyte Stimulator", Science. Jul. 9, 1999, vol. 285, No. 5425, pp. 260-263.

Pitti et al., "Genomic Amplification of a Decoy Receptor for Fas Ligand in Lung and Colon Cancer", Nature. vol. 396. Dec. 17, 1998, pp. 699-703.

Schneider et al., "BAFF, A Novel Ligand of the Tumor Necrosis Factor Family, Stimulates B Cell Growth", J. Exp. Med., vol. 189, No. 11, Jun. 7, 1999, pp. 1747-1756.

Shu et al., "B Cell Maturation Protein is a Receptor for the Tumor Necrosis Factor Family Member TALL-1", PNAS. vol. 97, No. 16, Aug. 1, 2000. pp. 9156-9161.

Thompson et al., "BAFF Interacts with the Orphan Receptor, BCMA", Scandinavian Journal of Immunology. vol. 51 (Supplement 1), 2000. p. 65.

Thompson et al., "BAFF Binds to the Tumor Necrosis Factor Receptor-like Molecule B Cell Maturation Antigen and is Important for Maintaining the Peripheral B Cell Population", J. Exp. Med., vol. 192. No. 1, Jul. 3, 2000. pp. 129-135.

Xia et al., "TACI is a TRAF-Interacting Receptor for TALL-1, a Tumor Necrosis Factor Family Member Involved in B Cell Regulation", J. Exp. Med., vol. 192, No. 1, Jul. 3, 2000, pp. 137-143.

Yu et al., "APRIL and TALL-1 and Receptors BCMA and TACI: System for Regulating Humoral Immunity", Nature Immunology, vol. 1, No. 3, Sep. 2000, pp. 252-256.

Kashii, Y. et al., "Constitutive Expression and Role of the TNF Family Ligands in Apoptotic Killing of Tumor Cells by Human NK Cells," J. Immunol. 163:5358-66. (1999).

Ward, P. and Mulligan, M. "Blocking of Adhesion Molecules in vivo as Anti-Imflammatory Therapy," Ther. Immunol. 1:165-71 (1994).

Ware, C., "APRIL and BAFF Connect Autoimmunity and Cancer," J. Exp. Med. 192:F35-F37 (2000).

von Bulow & Bram, "NF-AT Activation Induced by a CAML-Interacting Member of the Tumor Necrosis Factor Receptor Superfamily," Science 278:138-141 (1997).

\* cited by examiner

FIG. 1

Map of myc-murine APRIL construct pCCM213.10 for expression in Pichia pastoris

FIG. 2

Map Of Flag-Human APRIL Construct PS429 For Expression In Mammalian Cells

FIG. 3A Nucleotide sequence (sequence ID #7) and amino acid sequence (sequence id #8) of full length human BCMA.

sequence ID#7
1 atgttgcagatggctgggcagtgctccagtcaaaatgaatatttgacagtttgttgcatgcttgcatacctgt
tacaacgtctaccgacccgtcacgagggtttacttataaaactgtcaaacaacgtatgaaca sequence ID#8
1> M L Q M A G Q C S Q N E Y F D S L L H A C I P C 73 caacttcgatgtttctctaatactcctcctctaacatgtcagcgttattgtaatgcaagtgtgaccaattca
gttgaagctacaagaagattatgagagagattgtacagtcgcaataacattacgttcacactgttaagt

25> Q L R C S S N T P P L T C Q R Y C N A S V T N S

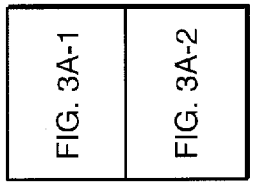

FIG. 3A-1

```
145  gtgaaggaacgaatgcgattctctgacctgtttgggactgagcttaataatttctttggcagtttcgtg
     cactttcctgcttacgctaagagacctggacaaaccctgactcgaattattaaagaaccgtcaaagcac

49> V  K  G  T  N  A  I  L  W  T  C  L  G  L  S  L  I  I  S  L  A  V  F  V 217  ctaatgttttgctaaggaagataagctctgaaccattaaaggacgagtttaaaaacacaggatcaggtctc
     gattacaaaacgattccttctattcgagacttggtaattcctgctcaaatttttgtcctagtccagag

73> L  M  F  L  L  R  K  I  S  S  E  P  L  K  D  E  F  K  N  T  G  S  G  L 289  ctgggcatggctaacattgacctggaaaagagcagaggactggtgatgaattattcttccgagaggcctcgag
     gacccgtaccgattgtaactgtacctttctgaccctcgtcctgaccactacttaataagaaggctctccggagctc

97> L  G  M  A  N  I  D  L  E  K  S  R  T  G  D  E  I  L  P  R  G  L  E 361  tacacggtggaagaatgcacctgtgaagactgcatcaagagcaaaccgaagtgcgactctgaccattgcttt
     atgtgccacctcttacgtggacacttctgactagttctcgtttggcttccagctgagactggtaacgaaa

121> Y  T  V  E  E  C  T  C  E  D  C  I  K  S  K  P  K  V  D  S  D  H  C  F 433  ccactcccagctatggaggaggcgcaaccattcttgtcaccacgaaaacgatgactattgcaagagcctg
     ggtgagggtcgatacctccctccgcgttggtaagaacagtggtgcttgctactgataacgttctcggac

145> P  L  P  A  M  E  E  G  A  T  I  L  V  T  T  K  T  N  D  Y  C  K  S  L 505  ccagctgcttgagtgctacggagatgagagaaatcaattctcttcttagttaaagacgatccatt
     ggtcgacgaaactacgatgcctctatctctttagttaagaaactgatccatt

|FIG. 3B-1|
|FIG. 3B-2|
|FIG. 3B-3|

FIG. 3B

```
  1 ATGGAGACAG ACACACTCCT GTTATGGGTG CTGCTGCTCT GGGTTCCAGG TTCCACTGGT
 >1  M  E  T   D  T  L  L   V  M  G  V   L  L  L  W    V  P  G   S  T  G
 61 GACGTCACGA TGTTGCAGAT GGCTGGGCAG TGCTCCCAAA ATGAATATTT TGACAGTTTG
>21  D  V  T   M  L  Q  M   A  G  Q  C   S  Q  N  E    Y  F  D   S  L
121 TTGCATGCTT GCATACCTTG TCAACTTCGA TGTTCTTCTA ATACTCCTCC TCTAACATGT
>41  L  H  A   C  I  P  C   Q  L  R  C   S  S  N  T    P  P  L   T  C
181 CAGCGTTATT GTAATGCAAG TCAGTGAAAG GAGTCGACAA AACTCACACA
>61  Q  R  Y   C  N  A  S   V  T  N  S   V  K  G  V    D  K  T   H  T
241 TGCCCACCGT GCCCAGCACC TGAACTCCTG GGGGGACCGT CAGTCTTCCT CTTCCCCCCA
>81  C  P  P   C  P  A  P   E  L  L  G   G  P  S  V    F  L  F   P  P
```

FIG. 3B-1

```
301 AAACCCAAGG ACACCCTCAT GATCTCCCGG ACCCCTGAGG TCACATGCGT GGTGGTGGAC
>101  K  P  K   D  T  L  M    I  S  R   T  P  E   V  T  C  V   V  V  D

361 GTGAGCCACG AAGACCCTGA GGTCAAGTTC AACTGGTACG TGGACGGCGT GGAGGTGCAT
>121  V  S  H   E  D  P  E    V  K  F   N  W  Y   V  D  G  V   E  V  H

421 AATGCCAAGA CAAAGCCGCG GGAGGAGCAG TACAACAGCA CGTACCGTGT GGTCAGCGTC
>141  N  A  K   T  K  P  R    E  E  Q   Y  N  S   T  Y  R  V   V  S  V

481 CTCACCGTCC TGCACCAGGA CTGGCTGAAT GGCAAGGAGT ACAAGTGCAA GGTCTCCAAC
>161  L  T  V   L  H  Q  D    W  L  N   G  K  E   Y  K  C  K   V  S  N

541 AAAGCCCTCC CAGCCCCCAT CGAGAAAACC ATCTCCAAAG CCAAAGGGCA GCCCCGAGAA
>181  K  A  L   P  A  P  I    E  K  T   I  S  K   A  K  G  Q   P  R  E

601 CCACAGGTGT ACACCCTGCC CCCATCCCGG GATGAGCTGA CCAAGAACCA GGTCAGCCTG
>201  P  Q  V   Y  T  L  P    P  S  R   D  E  L   T  K  N  Q   V  S  L

661 ACCTGCCTGG TCAAAGGCTT CTATCCCAGC GACATCGCCG TGGAGTGGGA GAGCAATGGG
>221  T  C  L   V  K  G  F    Y  P  S   D  I  A   V  E  W  E   S  N  G
```

FIG. 3B-2

```
721 CAGCCGGAGA ACAACTACAA GACCACGCCT CCCGTGTTGG ACTCCGACGG CTCCTTCTTC
>241  Q  P  E  N  N  Y  K  T  T  P  P  V  L  D  S  D  G  S  F  F

781 CTCTACAGCA AGCTCACCGT GGACAAGAGC AGGTGGCAGC AGGGGAACGT CTTCTCATGC
>261  L  Y  S  K  L  T  V  D  K  S  R  W  Q  Q  G  N  V  F  S  C

841 TCCGTGATGC ATGAGGCTCT GCACAACCAC TACACGCAGA AGAGCCTCTC CCTGTCTCCC
>281  S  V  M  H  E  A  L  H  N  H  Y  T  Q  K  S  L  S  L  S  P

901 GGGAAA
>301  G  K
```

Fig. 3B: Example of a gene encoding a huBCMA-huIgG1 fusion protein. Origin of nucleotide and amino acid sequence for hBCMA-hIgG1 fusion protein from expression vector pJST538 is as follows: signal peptide derived from a murine Ig kappa cDNA is encoded nucleotides 1-66 (amino acids 1-22); cysteine rich domain of human BCMA is boxed and encoded by nucleotides 70-222 (amino acids 24-74); hIgG1 is encoded by nucleotides 226-909 (amino acids 76-302); noncritical residues were introduced at the cloning junctions (amino acids 23 and 75) Arrowhead indicates predicted site of signal sequence cleavage.

FIG. 3B-3

A: 450ngs APRIL + IRRELEVANT RABBIT SERA
B: RABBIT SERA 1532 CONTROL
C: 450ngs APRIL + R1532

A: UNSTAINED CELLS
B: RABBIT SERA 1532 CONTROL
C: 1ug RANK-L + R1532
D: 450ngs APRIL + R1532

A: 450ngs APRIL + IRRELEVANT RABBIT SERA
B: RABBIT SERA 1532 CONTROL
C: 450ngs APRIL + R1532

A: UNSTAINED CELLS
B: NO PROTEIN CONTROL + BIOTINYLATED M2 ANTI-FLAG mAb
C: 1ug/ml FLAG-APRIL + BIOTINYLATED ISOTYPE CONTROL mAb
D: 1ug/ml FLAG-APRIL + BIOTINYLATED MW ANTI-FLAG mAb

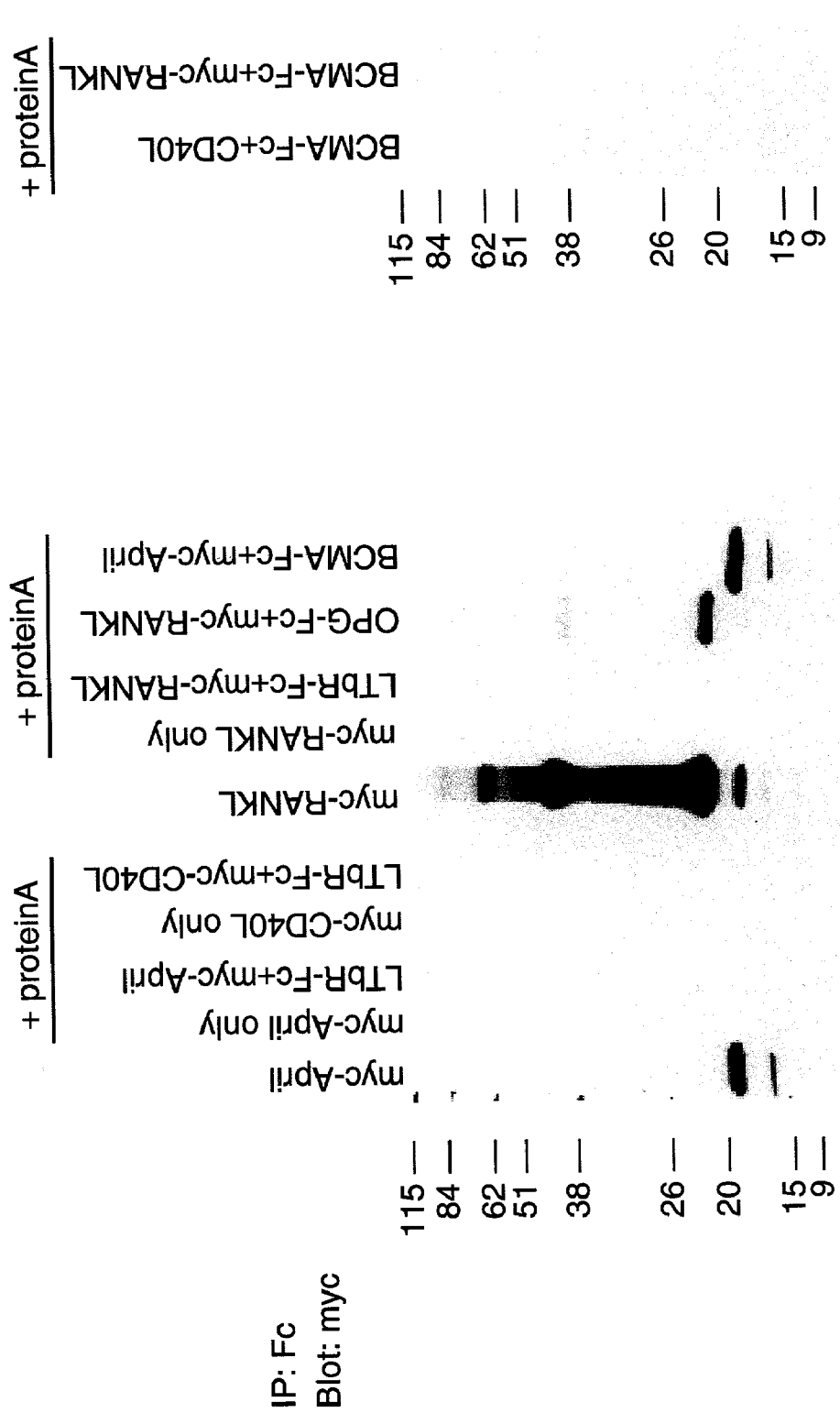

293EBNA CELLS TRANSFECTED WITH FULL LENGHT hBCMA WERE STAINED WITH 0, 40, 200, 1000, OR 5000 mg/ml myc-mAPRIL, RABBIT ANTI-APRIL ANTISERA (R1532), AND PE-LABELLED DONKEY ANTI-RABBIT IgG.

293EBNA CELLS TRANSFECTED WITH FULL LENGHT hBCMA WERE

A: RABBIT SERA (R1532) CONTROL
B: 200 ng/ml myc-mAPRIL + 1ug/ml DCMA-Ig
C: 200 ng/ml myc-mAPRIL

METHODS OF TREATING A TUMOR THAT EXPRESSES APRIL BY ADMINISTERING BCMA

RELATED APPLICATIONS

This is a continuation of PCT/US00/27579, filed on Oct. 5, 2000, which claims priority from U.S. provisional application Ser. No. 60/157,933 filed on Oct. 6, 1999, U.S. provisional application Ser. No. 60/181,807 filed 11 Feb. 2000 and U.S. provisional application Ser. No. 60/215,688 filed 30 Jun. 2000.

FIELD OF THE INVENTION

The present invention relates generally to methods of treatment for cancer. The methods involve the administration of certain tumor necrosis factor (TNF) antagonists.

BACKGROUND OF THE INVENTION

Members of the tumor-necrosis factor (TNF) family of cytokines are involved in an ever expanding array of critical biological functions. Each member of the TNF family acts by binding to one or more members of a parallel family of receptor proteins. These receptors in turn signal intracellularly to induce a wide range of physiological or developmental responses. Many of the receptor signals influence cell fate, and often trigger terminal differentiation. Examples of cellular differentiation include proliferation, maturation, migration, and death.

TNF family members are Type II membrane bound proteins, having a short intracellular N-terminal domain, a transmembrane domain, and the C-terminal receptor binding domains lying outside the cell surface. In some cases the extracellular portion of the protein is cleaved off, creating a secreted form of the cytokine. While the membrane bound proteins act locally, presumably through cell contact mediated interaction with their receptors, the secreted forms have the potential to circulate or diffuse, and therefore can act at distant sites. Both membrane bound and secreted forms exist as trimers, and are thought to transduce their signal to receptors by facilitating receptor clustering.

The TNF receptor protein family is characterized by having one or more cysteine rich extracellular domains. Each cysteine rich region creates a disulfide-bonded core domain, which contributes to the three dimensional structure that forms the ligand binding pocket. The receptors are Type I membrane bound proteins, in which the extracellular domain is encoded by the N-terminus, followed by a transmembrane domain and a C-terminal intracellular domain. The intracellular domain is responsible for receptor signaling. Some receptors contain an intracellular "death domain", which can signal cell apoptosis, and these can be strong inducers of cell death. Another class of receptors can weakly induce cell death; these appear to lack a death domain. A third class of receptors do not induce cell death. All classes of receptors can signal cell proliferation or differentiation instead of death, depending on cell type or the occurrence of other signals.

A well studied example of the pluripotent nature of TNF family activity is the nominant member, TNF. TNF can exist as a membrane bound cytokine or can be cleaved and secreted. Both forms bind to the two TNF receptors, TNF-R55 and TNF-R75. Originally described on the basis on its' ability to directly kill tumor cells, TNF also controls a wide array of immune processes, including inducing acute inflammatory reactions, as well as maintaining lymphoid tissue homeostasis. Because of the dual role this cytokine can play in various pathological settings, both agonist and antagonist reagents have been developed as modifiers of disease. For example TNF and LTα (which also signals through the TNF receptors) have been used in treatment for cancers, especially those residing in peripheral sites, such as limb sarcomas. In this setting direct signaling by the cytokine through the receptor induces tumor cell death (Aggarwal and Natarajan, 1996. Eur Cytokine Netw 7:93-124).

In immunological settings, agents that block TNF receptor signaling (e.g., anti-TNF mAb, soluble TNF-R fusion proteins) have been used to treat diseases like rheumatoid arthritis and inflammatory bowel disease. In these pathologies TNF acts to induce cell proliferation and effector function, thereby exacerbating autoimmune disease, and in this setting blocking TNF binding to its receptor(s) has therapeutic benefit (Beutler, 1999. J Rheumatol 26 Suppl 57:16-21).

A more recently discovered ligand/receptor system appears amenable to similar manipulations. Lymphotoxin beta (LTβ), a TNF family member which forms heterotrimers with LTα, bind to the LTβ-R. Some adenocarcinoma tumor cells which express LTβ-R can be killed or differentiated when treated with an agonistic anti-LTβ-R mAb (Browning et al., 1996. J Exp Med 183: 867-878). In immunological settings it has been shown that anti-LTβ mAb or soluble LTβ-R-Ig fusion protein can block the development of inflammatory bowel diseases, possibly by influencing dendritic cell and T cell interaction (Mackay et al., 1998. Gastroenterology 115:1464-1475).

The TRAIL system also has potential as a cancer therapy. TRAIL interacts with a number of membrane bound and soluble receptors. Two of these receptors, TRAIL-R1 and TRAIL R2 (also called DR4 and DR5), transmit death inducing signals to tumor cells but not to normal cells, which express additional TRAIL receptors that do not induce death. These additional receptors are thought to function as decoys. The use of soluble TRAIL to kill tumor cells relies on the selective expression of decoy receptors on normal but tumor tissue (Gura, 1997. Science 277: 768).

Tumor cells themselves often express a variety of decoy receptors that block immune recognition or effector functions. Indeed some tumors overexpress TRAIL decoy receptors, apparently to avoid TRAIL mediated death (Sheikh et al., 1999. Oncogene 18: 4153-4159). This limits the utility of TRAIL as an anti-tumor agent in some settings. Similar observations have been made about a decoy receptor for FAS-L, which is overexpressed by lung and colon cancer cells (Pitti et al., 1998. Nature 396: 699-703), and for the IL-1 receptor antagonist (Mantovani et al., 1998. Ann. N Y Acad. Sci. 840: 338-351). Decoy receptors are also employed by viral genomes to protect infected host cells from host defense mechanisms.

APRIL (A Proliferation Inducing Ligand) is a new member of the TNF family of proteins. APRIL expression and functional studies suggest that this protein is utilized by tumor cells to induce rapid proliferation. Tumor cell lines treated with soluble APRIL protein or transfected with APRIL cDNA grow rapidly in vitro. APRIL transfected cells implanted into immunodeficient mice grow rapidly as tumors. Finally, human tumor cells, but not normal tissue, express high levels of APRIL messenger RNA. These observations suggest that APRIL binds to a receptor that is also expressed by tumor cells, setting up autocrine or paracrine tumor cell activation. In addition, it is possible that APRIL acts in other disease settings, such that activating or blocking the APRIL pathway would have additional utility. For example, underexpression or overexpression of APRIL may play a role in developmental defects, since development is often characterized by the carefully controlled balance between cell proliferation and cell death. Similarly, APRIL may act in cell proliferative diseases, such as those that occur in connection with some autoimmune diseases (e.g., lupus) or in inflammatory diseases where cell populations expand rapidly (e.g., bacterial sepsis).

Based on the known utility of using agonists and antagonists of TNF and TNF receptor family members as disease modifiers, the APRIL pathway presents itself as an important target for drug development. This is particularly true for cancer therapy since tumor cells appear to produce and utilize APRIL to support their own growth, and are therefore unlikely to produce decoy receptors or other antagonists of the APRIL pathway. Thus the APRIL pathway is uniquely different from, for example, the TRAIL or FAS-L pathways, which can be thwarted by tumor decoy receptors.

Current treatments for cancer are inadequate for many tumor types, due to poor efficacy, low impact on survivorship, toxicity that causes severe side effects, or combinations thereof. Therefore there is a need to identify and develop additional methods for treating cancer growth which can provide efficacy without inducing severe side effects. Antagonists of the APRIL pathway, including anti-APRIL mAbs, anti-APRIL receptor mAbs, soluble APRIL receptor-Ig fusion proteins, natural antagonists, small molecule antagonists, and chemical, pharmaceutical, or other antagonists would thus be useful.

To this end we have identified B cell mediated protein (BCM or BCMA) as a receptor for APRIL.

SUMMARY OF THE INVENTION

Applicants have found that BCMA is a receptor for the tumor necrosis factor, APRIL. APRIL is the same molecule previously described in WO 99 12965, which is incorporated by reference herein. The APRIL receptor is referred to hereinafter as "APRIL-R". The present invention is directed to methods of treatment and pharmaceutical preparations for use in the treatment of mammalian species having or at risk of having cancer. Such subjects include subjects already afflicted with cancer, or which have already received cancer therapy.

The methods and compositions of this invention capitalize in part upon the discovery that certain agents that are cancer therapeutic agents, defined herein as APRIL-R antagonists, including for example, anti-APRIL-R antibodies, may be used in the treatment of subjects at risk of developing cancer as defined herein or the need for cancer treatment.

The cancer therapeutic agents of the invention may be administered by any route of administration which is compatible with the selected agent, and may be formulated with any pharmaceutically acceptable carrier appropriate to the route of administration. Preferred routes of administration are parenteral and, in particular, intravenous, intraperitoneal, and intracapsular. Treatments are also preferably conducted over an extended period on an outpatient basis. Daily dosages of the cancer therapeutic agents are expected to be in the range of about 0.01-1000 µg/kg body weight, and more preferably about 10-300 µg/kg body weight, although precise dosages will vary depending upon the particular cancer therapeutic agent employed and the particular subject's medical condition and history.

The treatments of the present invention are useful in eradicating a substantially clonal population (colony) of transformed cells from the body of a mammal, or to suppress or to attenuate the growth of the colony, which is most commonly referred to as a tumor. As such they are useful in prolonging the lives, and in maintaining the quality of life, of subjects at risk of, or already afflicted with cancer.

BRIEF DESCRIPTION OF THE DRAWINGS

FIG. 8 shows immunoprecipitation of myc-mAPRIL using BCMA-Fc fusion protein. FIG. 8A shows specific hBCMA-Fc/myc-mAPRIL and positive control OPG-Fc/Rank-1 immunoprecipitations, compared to negative controls shown in FIG. 8B.

Figure 4A:
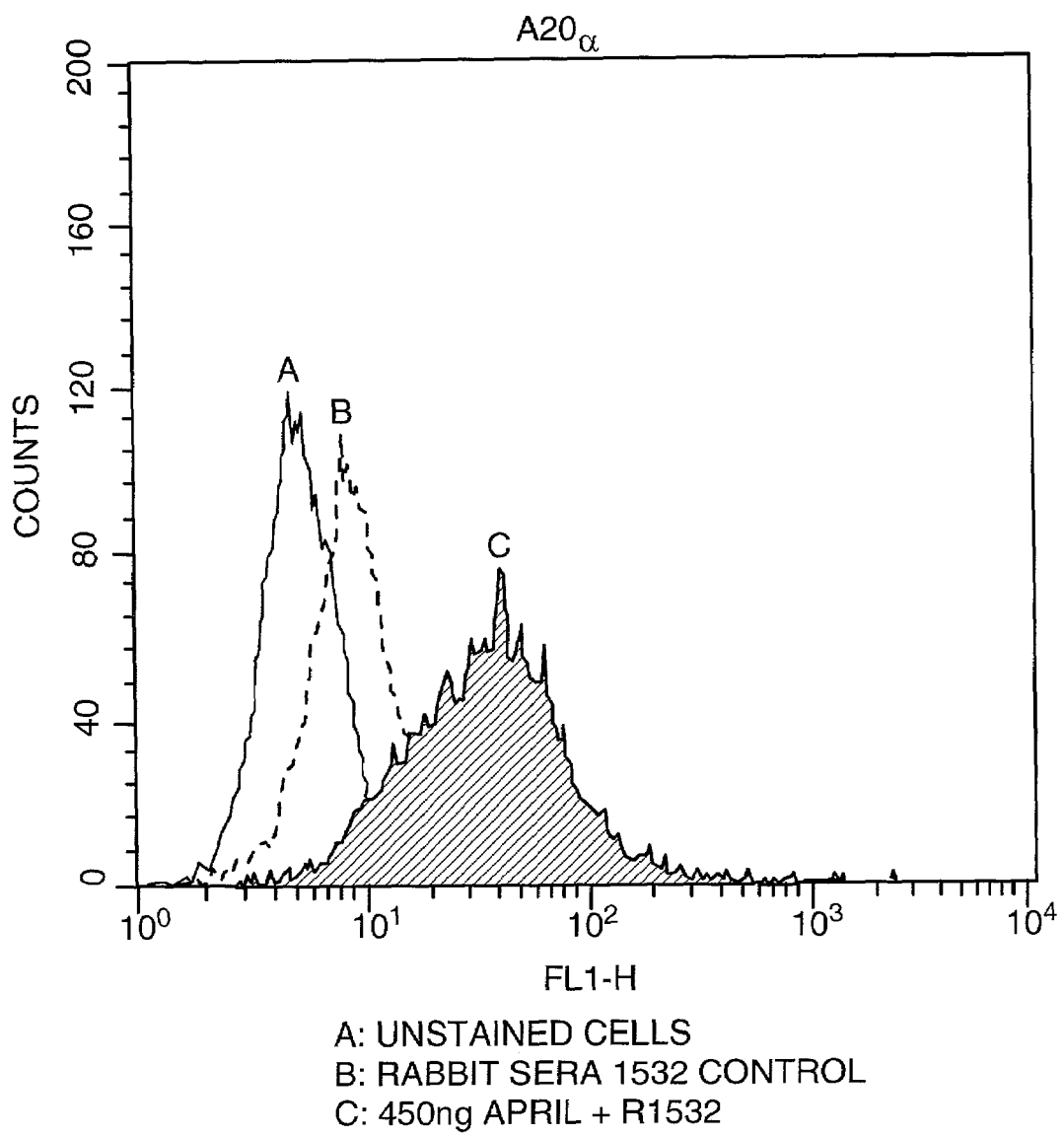
FIG. 4 shows binding of myc-murine APRIL to the murine B cell lymphoma line A20. 3 separate experiments show specific binding of APRIL to A20 cells compared to A) unstained cells and cells stained with R1532 only, B) cells stained with RANKL-L and R1532 and C) cells stained with APRIL and an irrelevant rabbit sera.
Figure 4B:
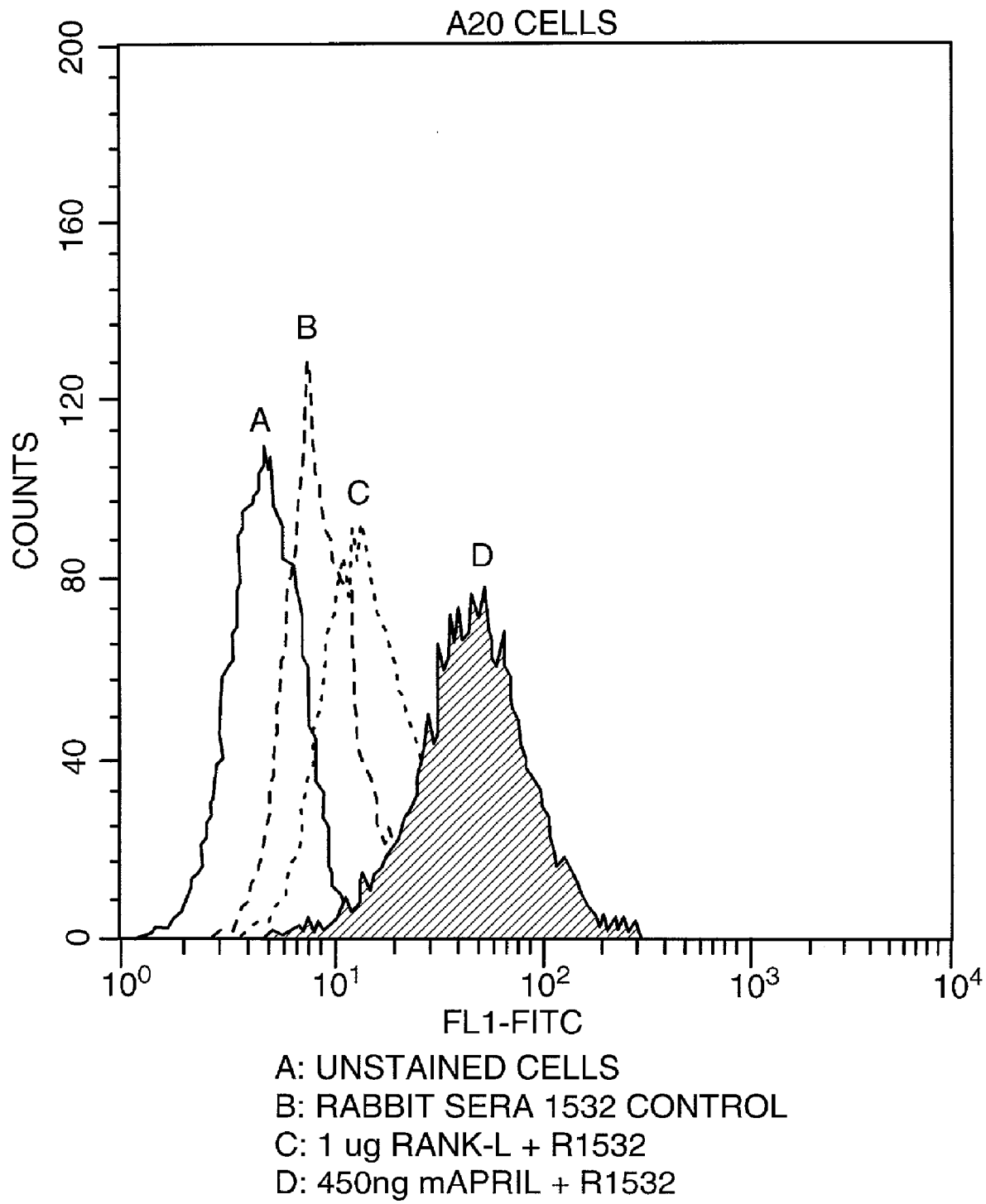
Figure 4C:
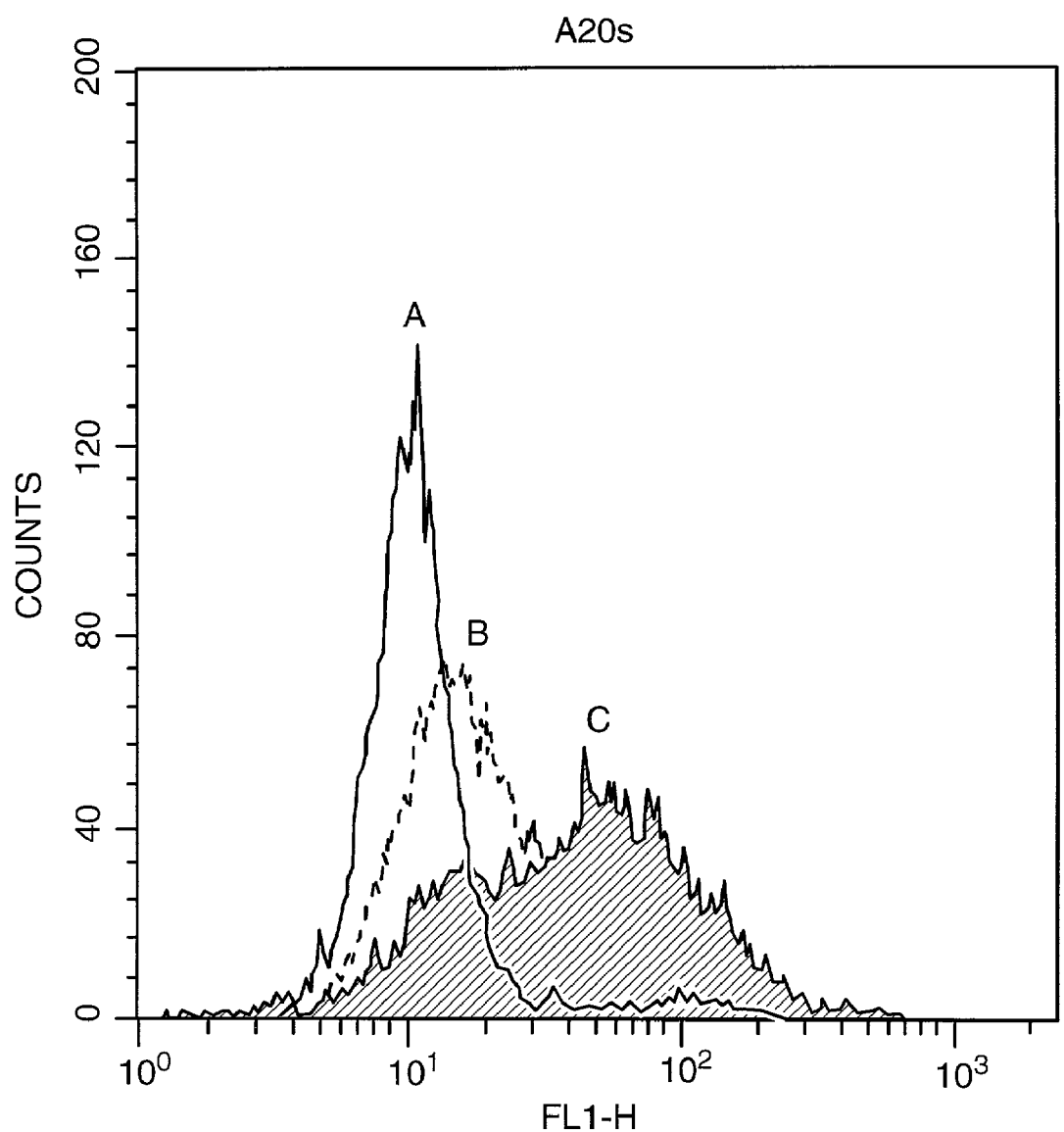
Figure 5A:
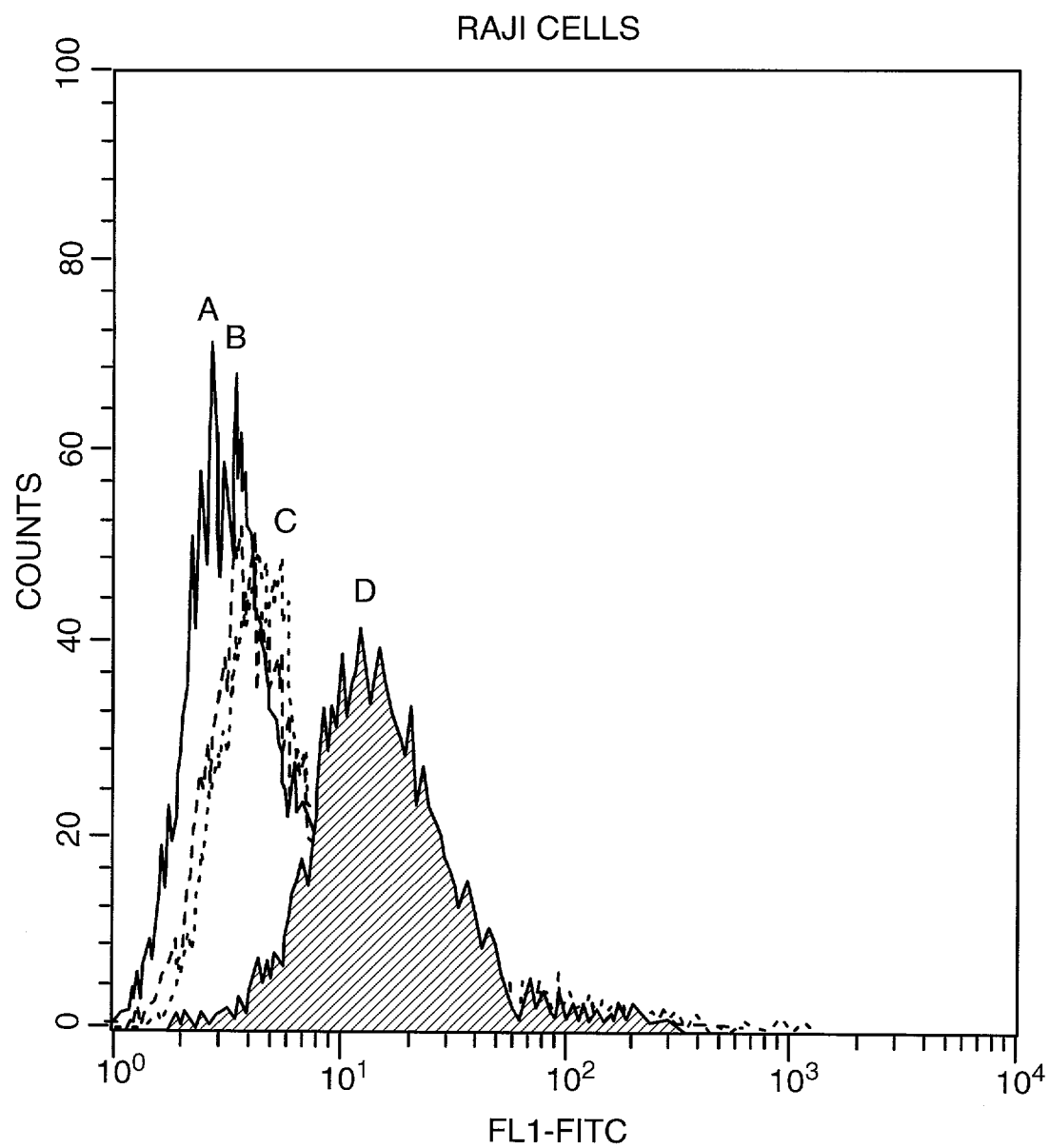
FIG. 5 shows binding of myc-murine APRIL to the human B cell lymphoma line RAJI. 2 separate experiments show specific binding of APRIL to RAJI cells compared to A) unstained cells and cells stained with R1532 only, and cells stained with RANK-1 and R1532 and B) cells stained with APRIL and an irrelevant rabbit sera
Figure 5B:
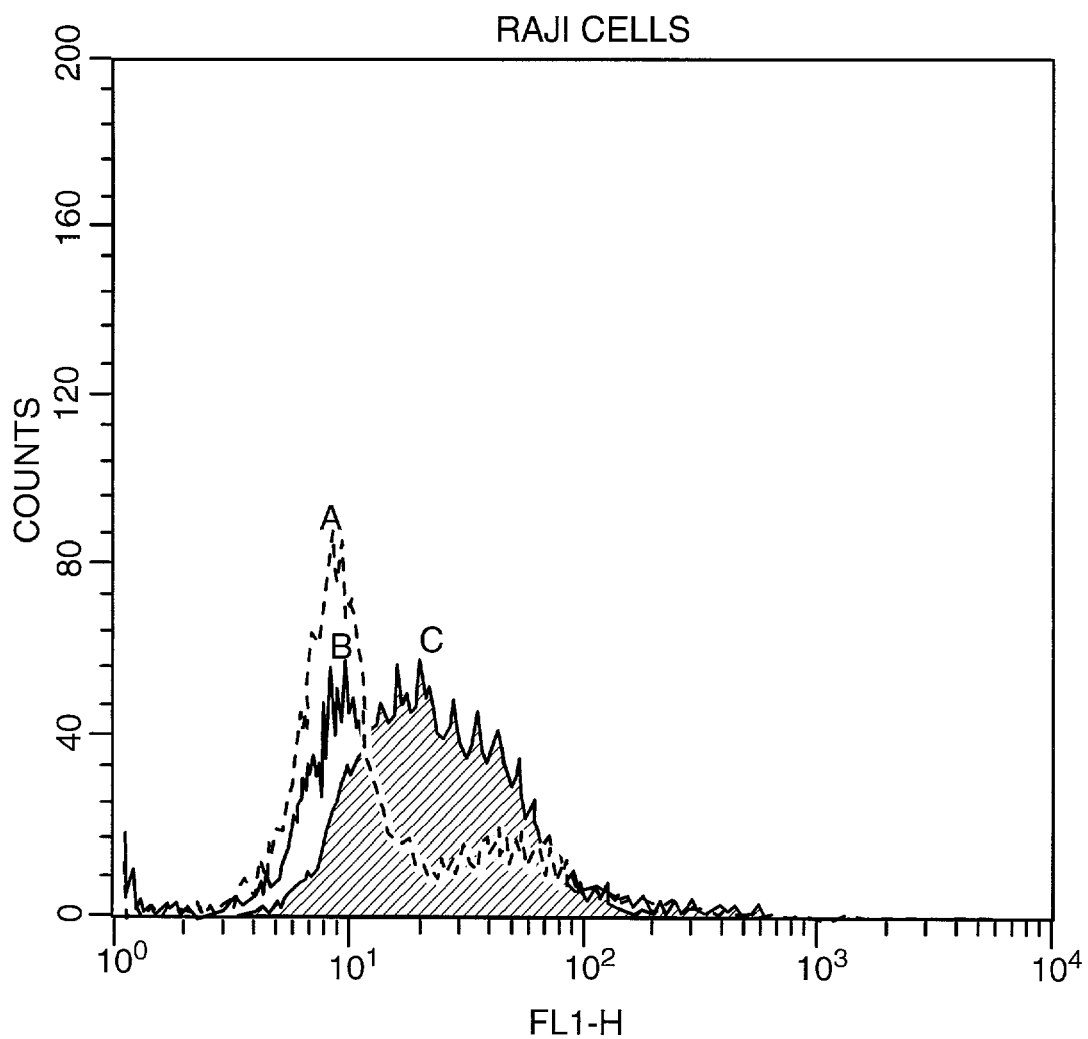
Figure 6A:
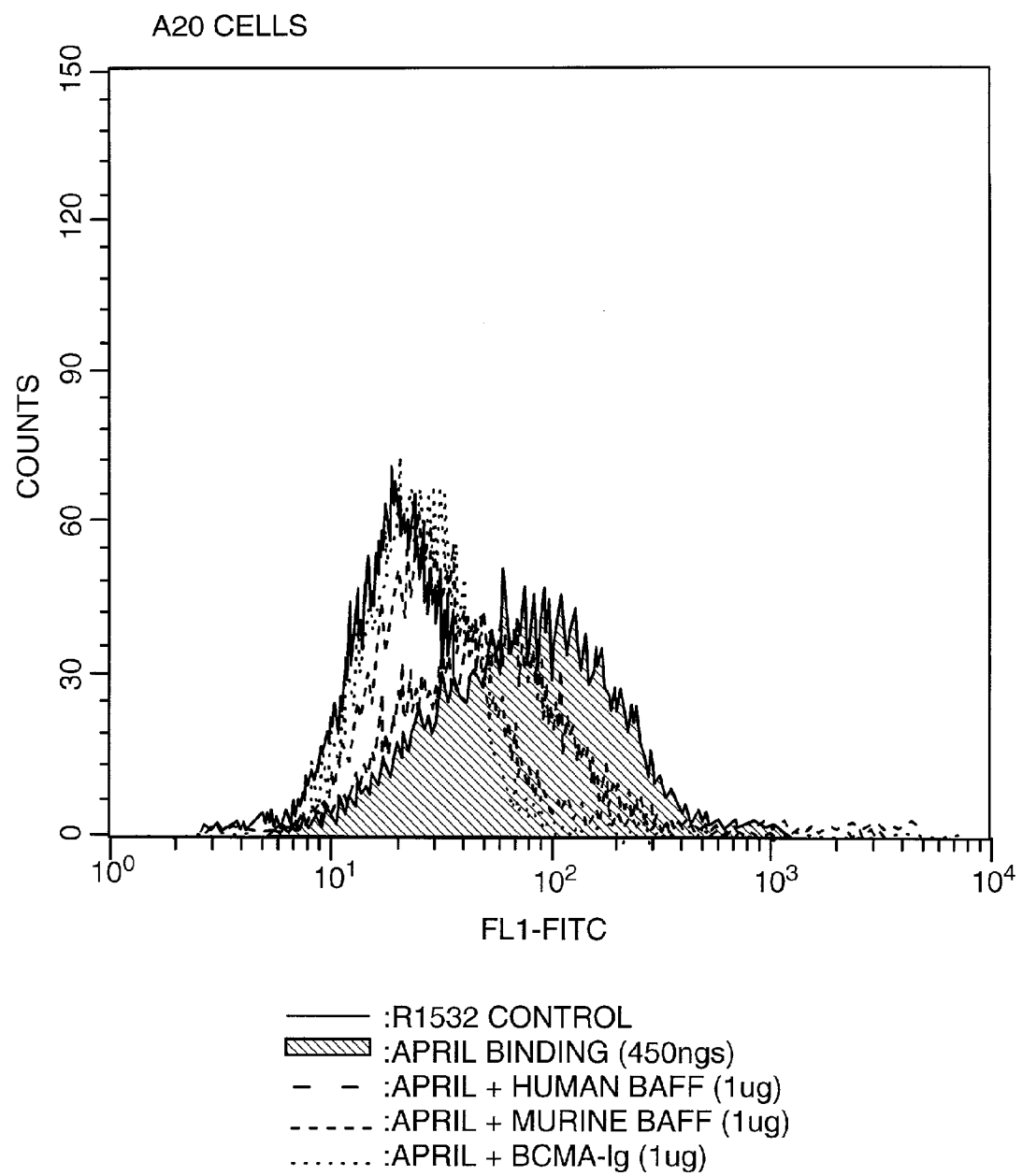
FIG. 6 shows that APRIL binding to A20 cells (A) and Raji cells (B) is competed using soluble BAFF protein or soluble BCMA-Ig protein.
Figure 6B:
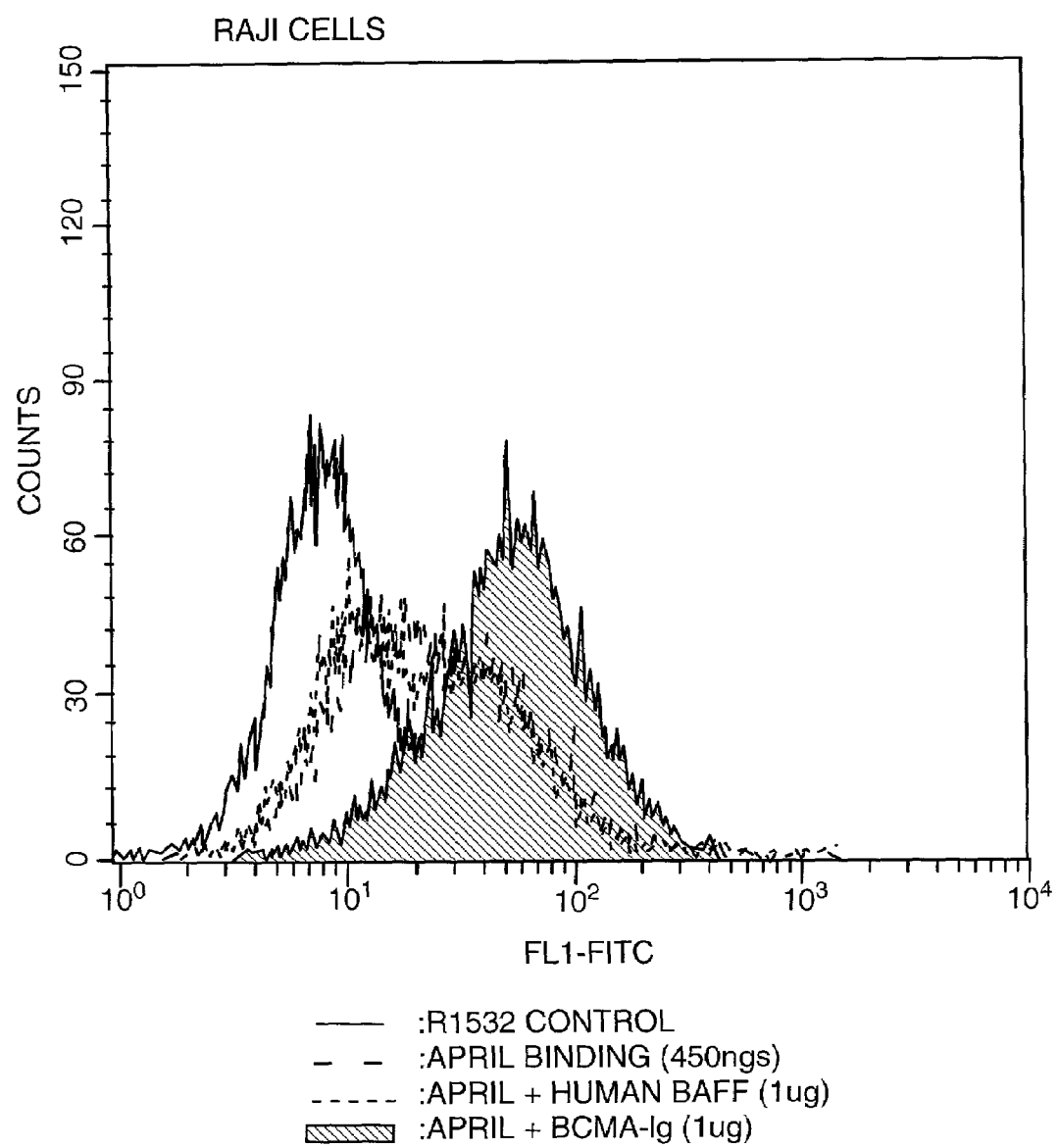
Figure 7A:
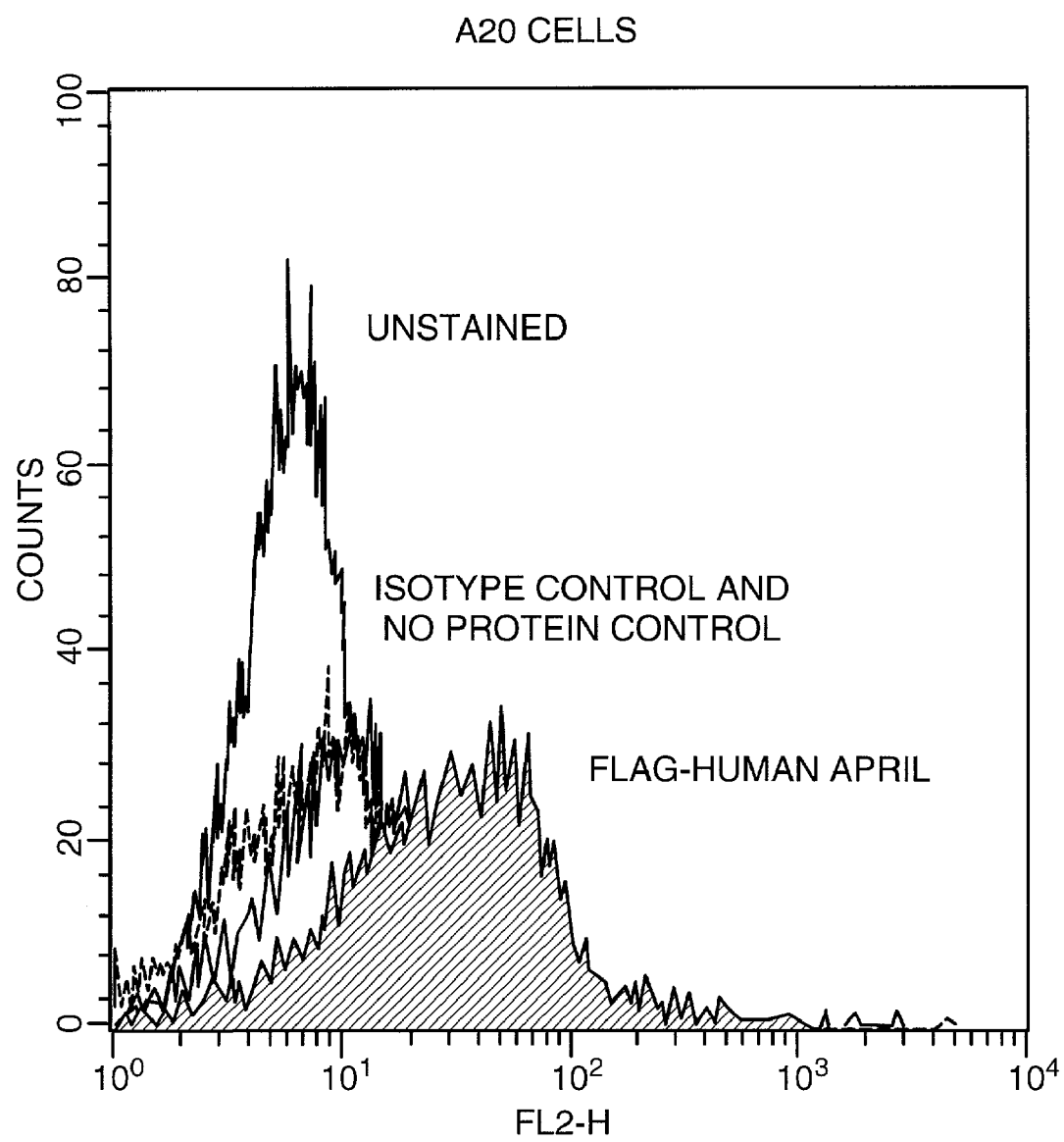
FIG. 7 shows binding of FLAG-human APRIL to various cell lines: A) A20 cells, B) HT29 cells, C)NIH3T3 cells. Specific binding is demonstrated using biotinylated anti-FLAG mAb M2 detection compared to binding seen with an irrelevant isotype control mAb or without addition of FLAG-APRIL.
Figure 7B:
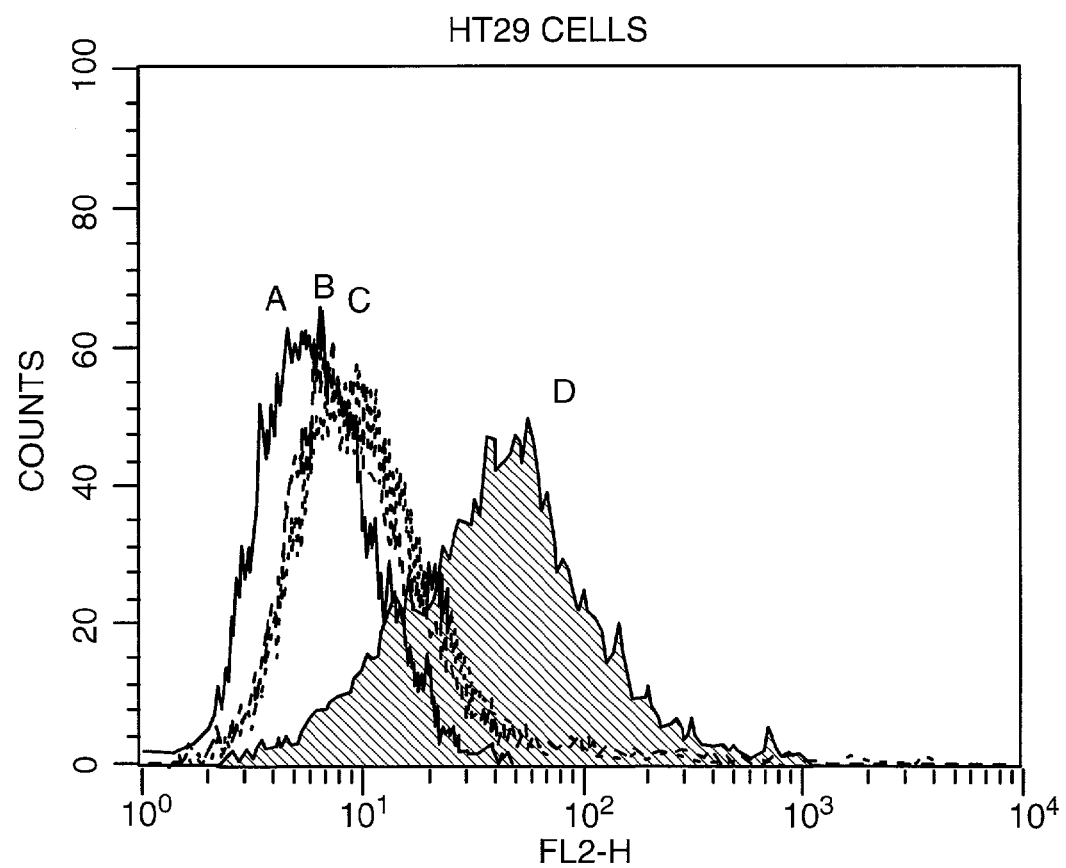
Figure 7C:
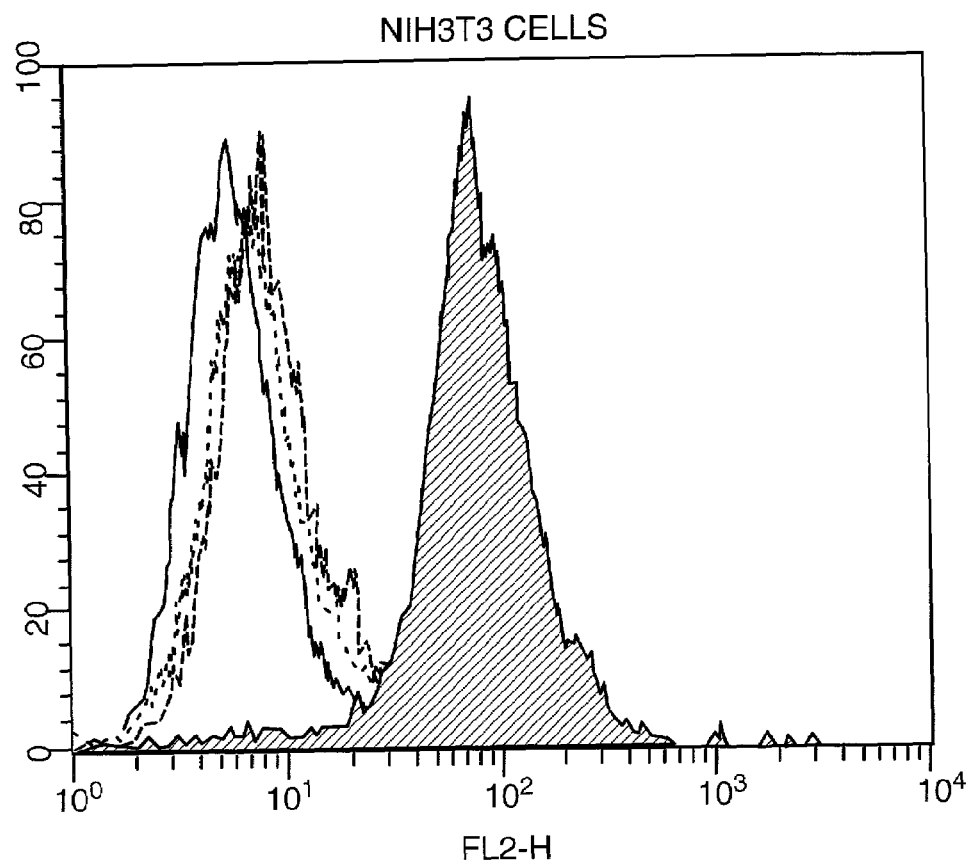
Figures 8C, 8D:
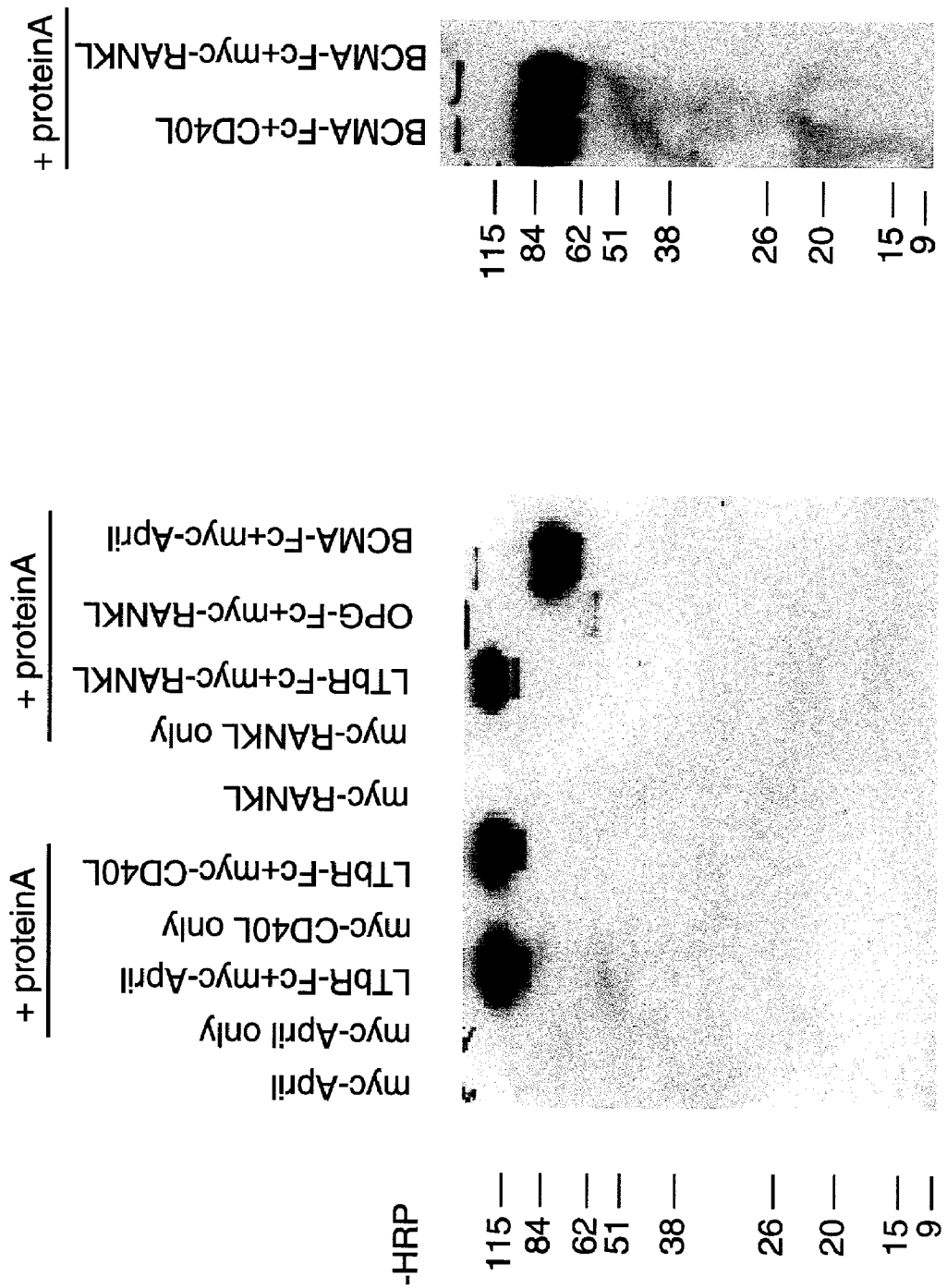
FIGS. 8C and 8D demonstrate that the amounts of protein loaded were equivalent.
Figures 1, 9A:
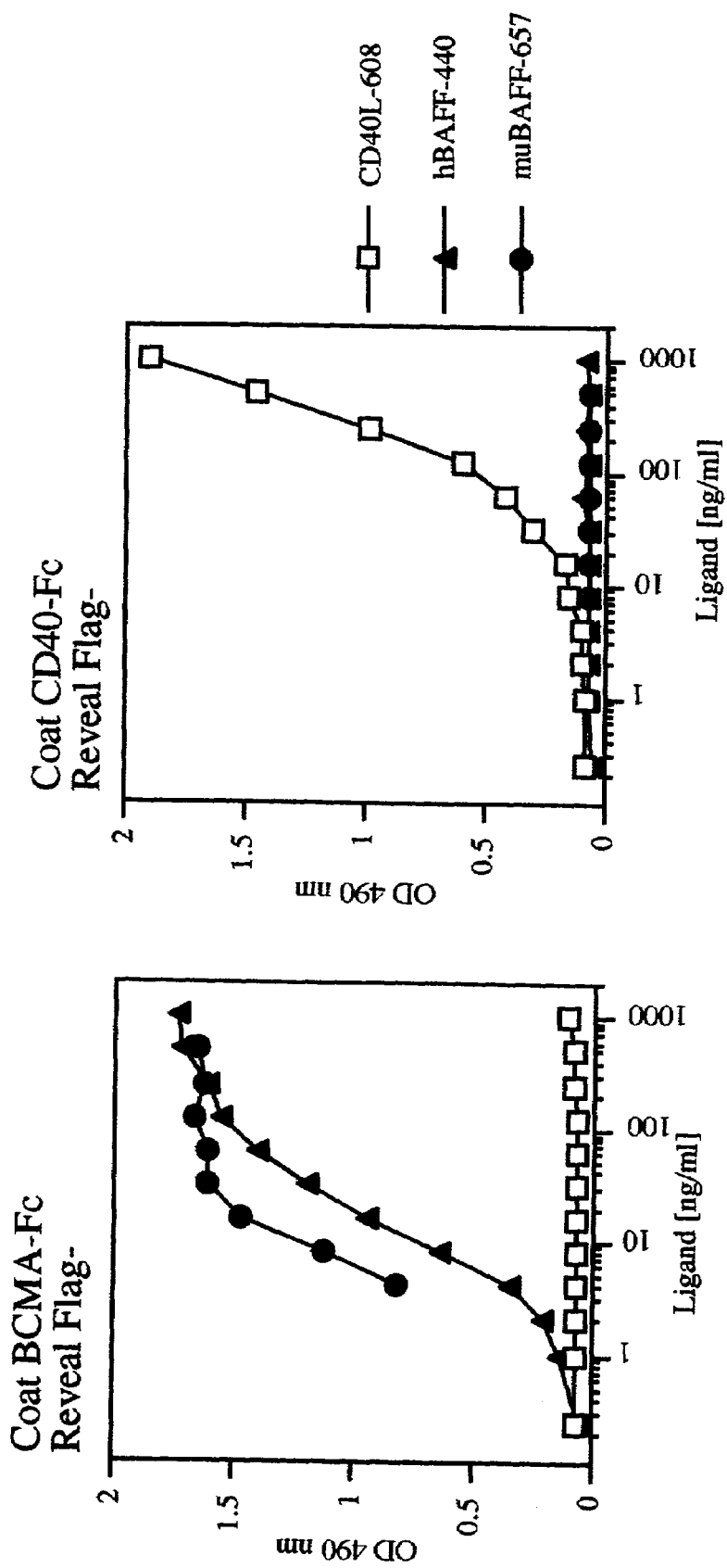
FIG. 1 shows the nucleic acid sequence (SEQ ID NO:1) of a cDNA for murine APRIL and its derived amino acid sequence (SEQ ID NO:3) as mapped in vector pCCM213.10. Shown underlined is the myc epitope and the amino acids derived from FasL. The beginning of APRIL extracellular domain coding sequence is indicated by arrows.
Figures 2, 9A:
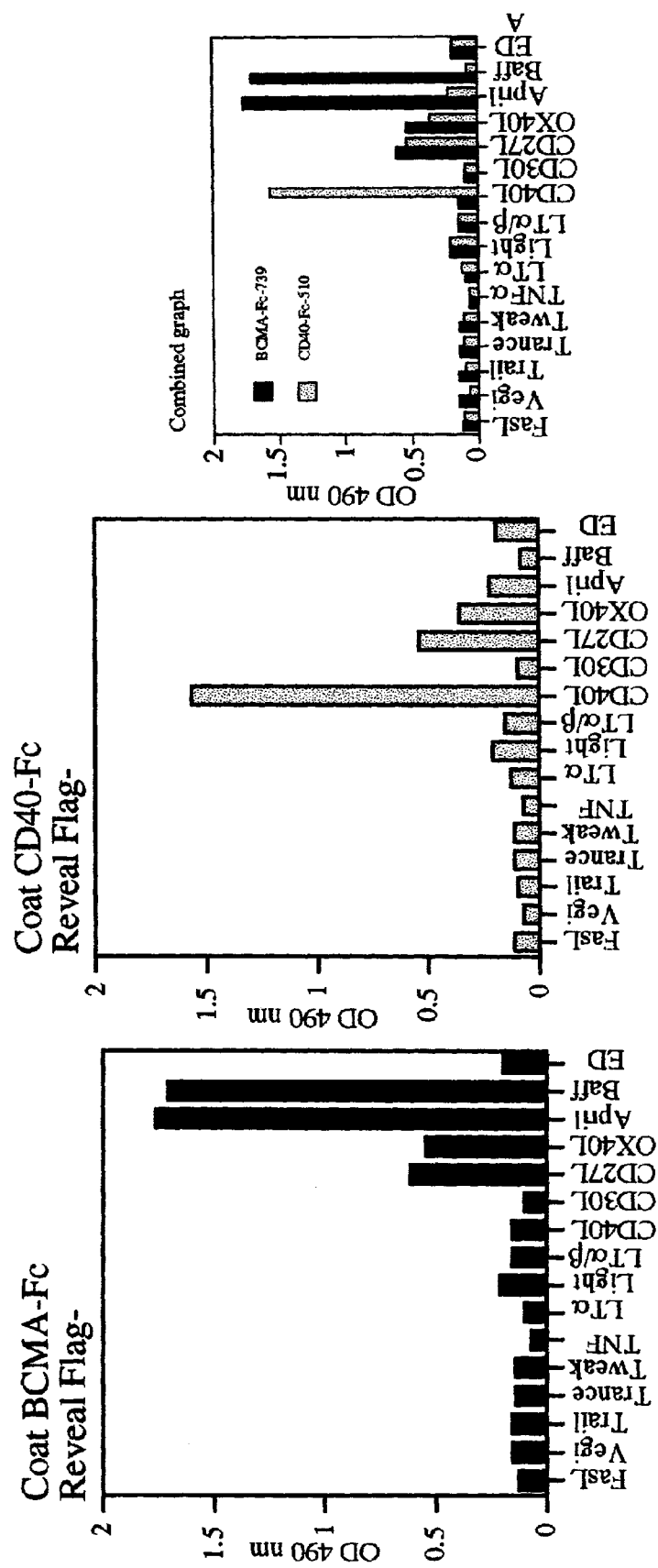
FIG. 2 shows the nucleic acid sequence (SEQ ID NO:4) and its derived amino acid sequence (SEQ ID NO:6) of FLAG-human APRIL construct for expression in mammalian cells. The map indicates the signal sequence (1-15); the FLAG epitope (AA 16-23) and the beginning of human APRIL extracellular domain coding sequence (32-end).
Figures 1, 9B:
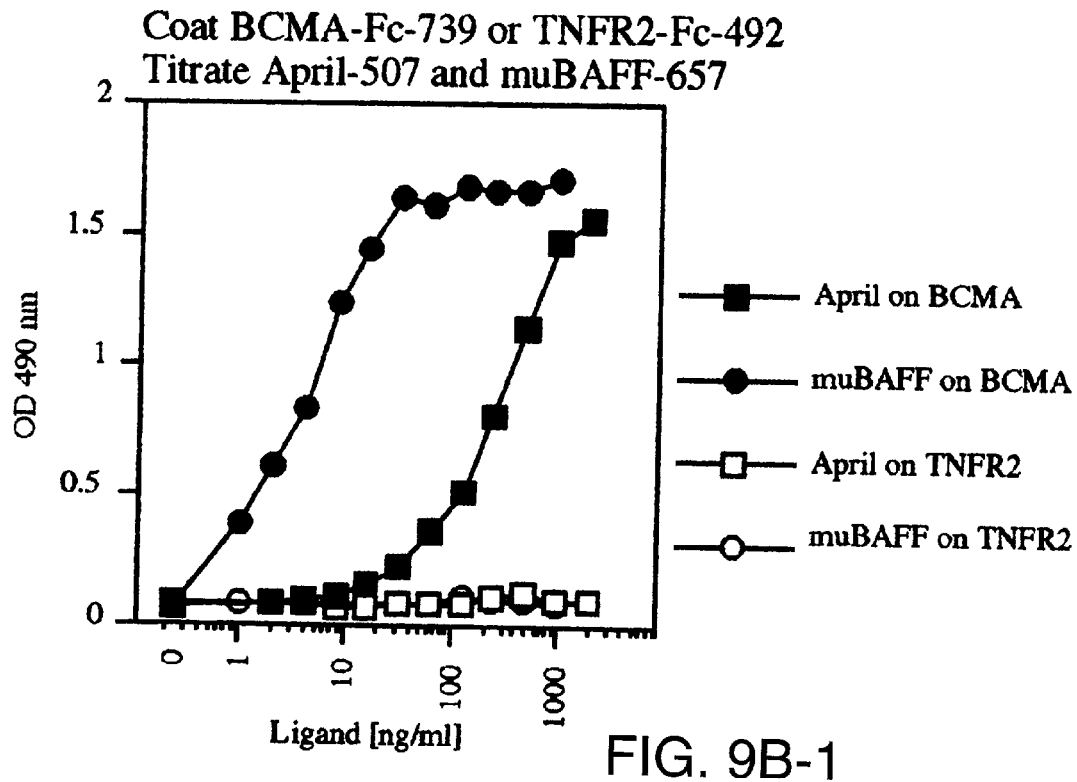
Figures 2, 9B:
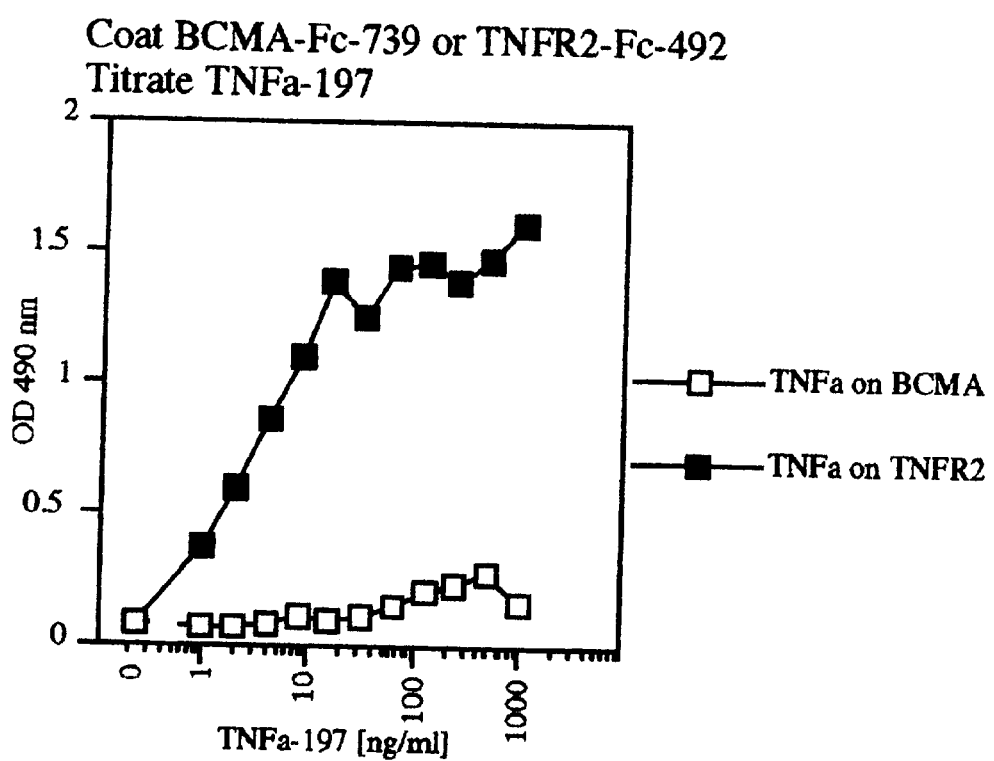
Figures 3, 9B:
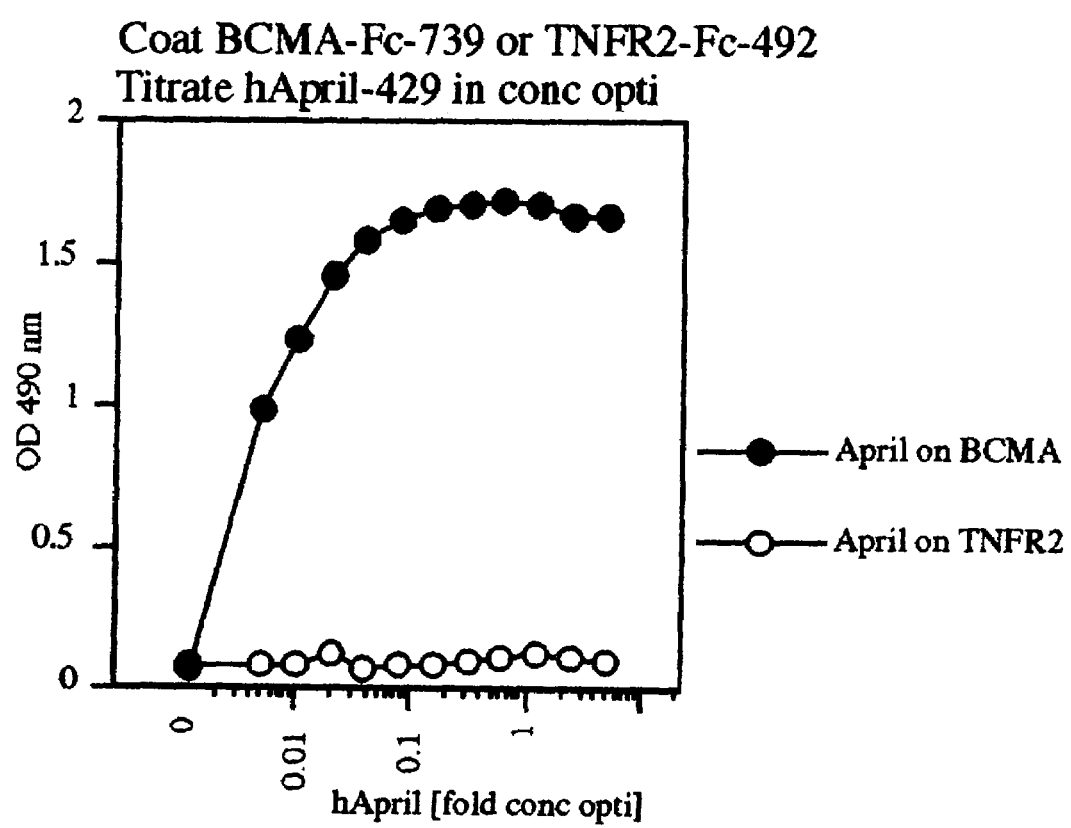
FIG. 3A shows the nucleic acid sequence (SEQ ID NO:7) and amino acid sequence (SEQ ID NO:8) of full length human BCMA.
FIG. 3B shows the nucleic acid sequence (SEQ ID NO:11) of pJST538, a plasmid encoding a human APRIL-R-hIgGFc fusion construct and its derived amino acid sequence (SEQ ID NO:12).
FIG. 9 shows an ELISA format experiments demonstrating that FLAG-h APRIL binds to hBCMA-fc fusion protein. Various receptor-Fc fusion proteins were coated onto the ELISA plates and bound with FLAG-tagged ligands. A)Detection of the bound ligands revealed that only APRIL and hBAFF specifically bind to hBCMA-Fc, but not hCD40-Fc. B) Dose titration showing that the ELISA signal detected after binding hAPRIL or hBAFF onto hBCMA-Fc coated plates is linearly dependent on the amount of protein added.
Figure 10:
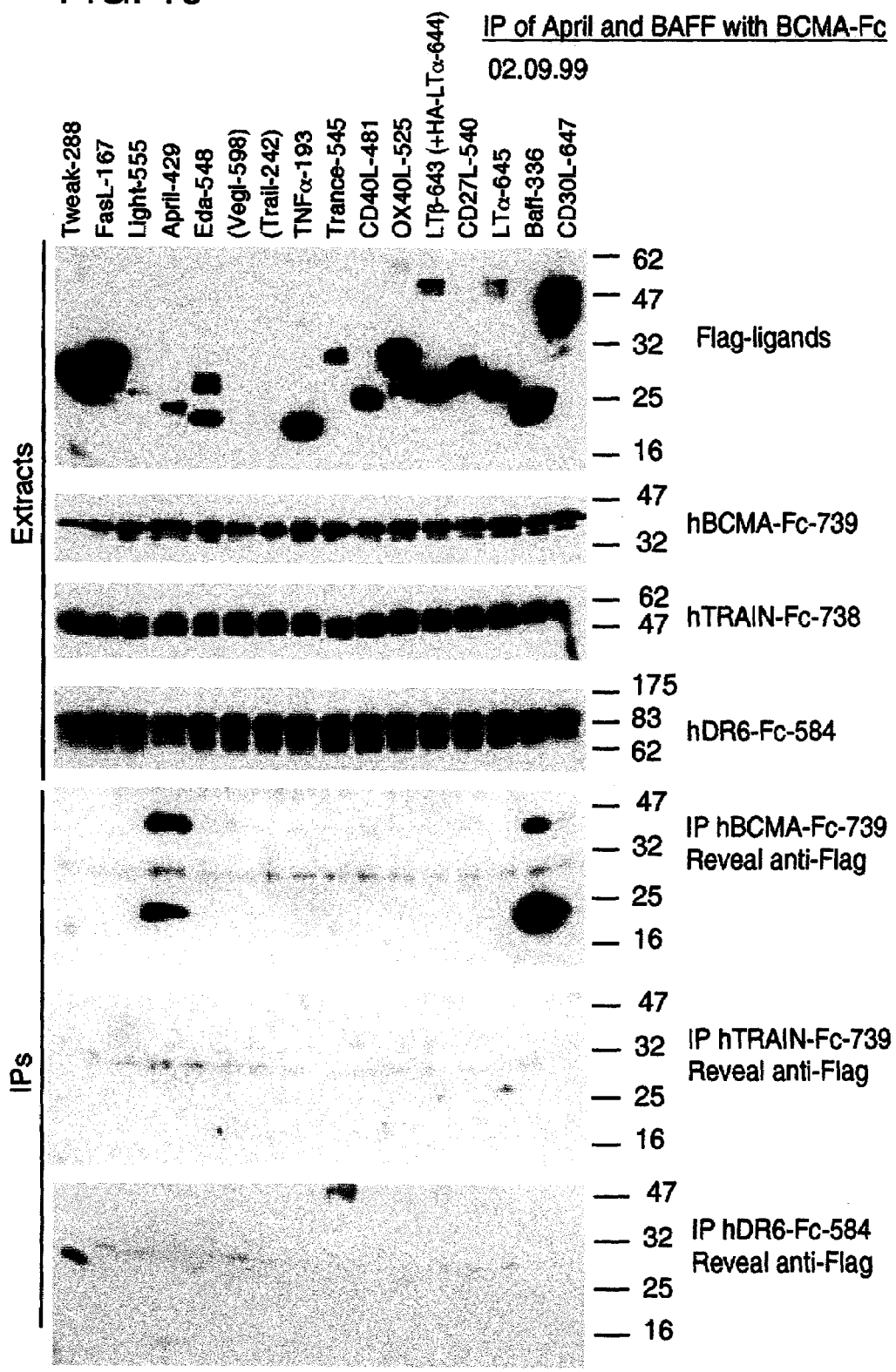
FIG. 10 show an immunoprecipitation of FLAG-hAPRIL and FLAG-HBAFF by hBMCA-Fc fusion protein. Upper 4 panels show the equivalence of the protein loads in each immunoprecipitation, while the lower panels show that hAPRIL and hBAFF are immunoprecipitated by hBCMA-Fc but not hTRAIN-Fc.
Figure 11A:
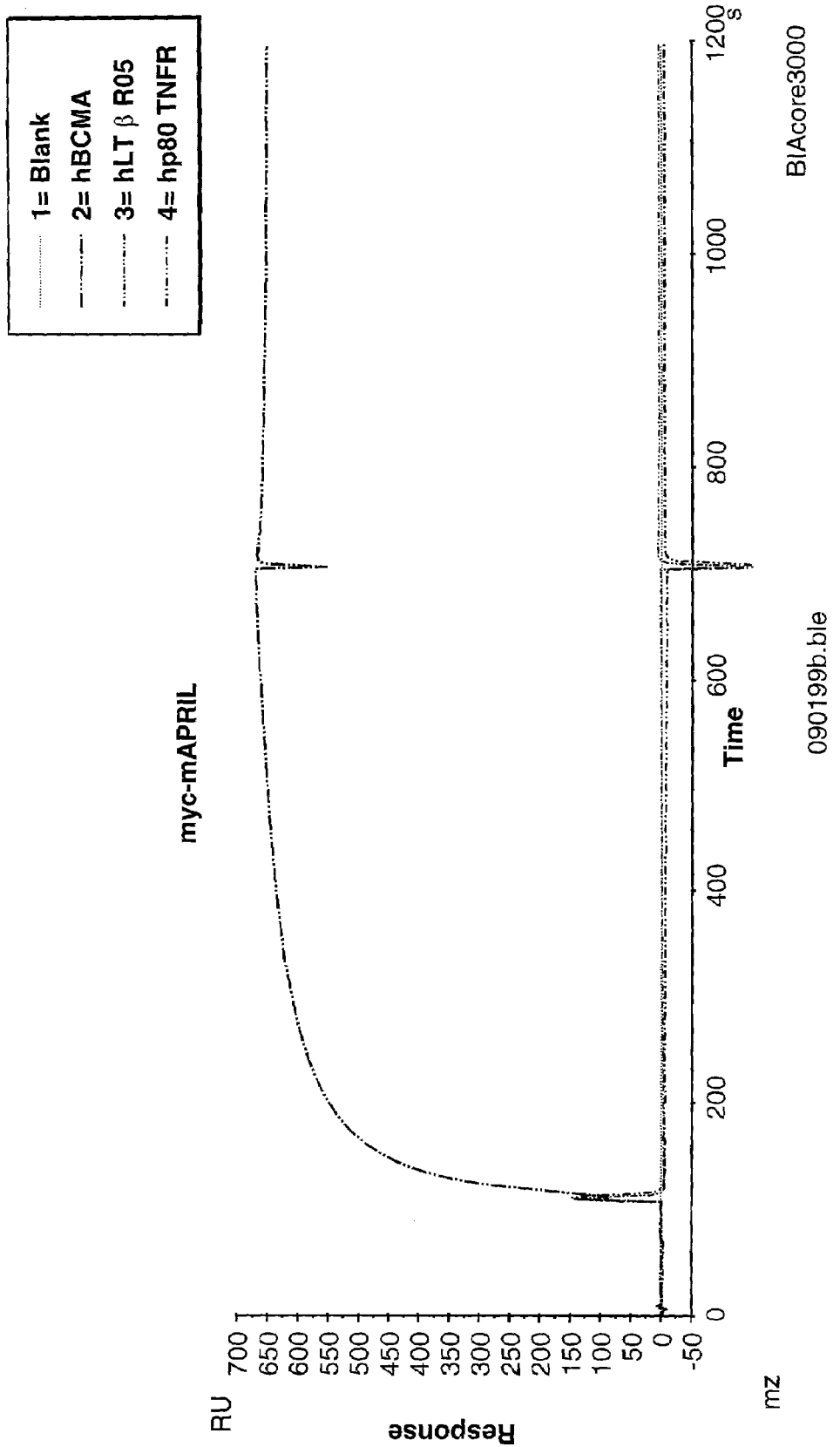
Figure 11B:
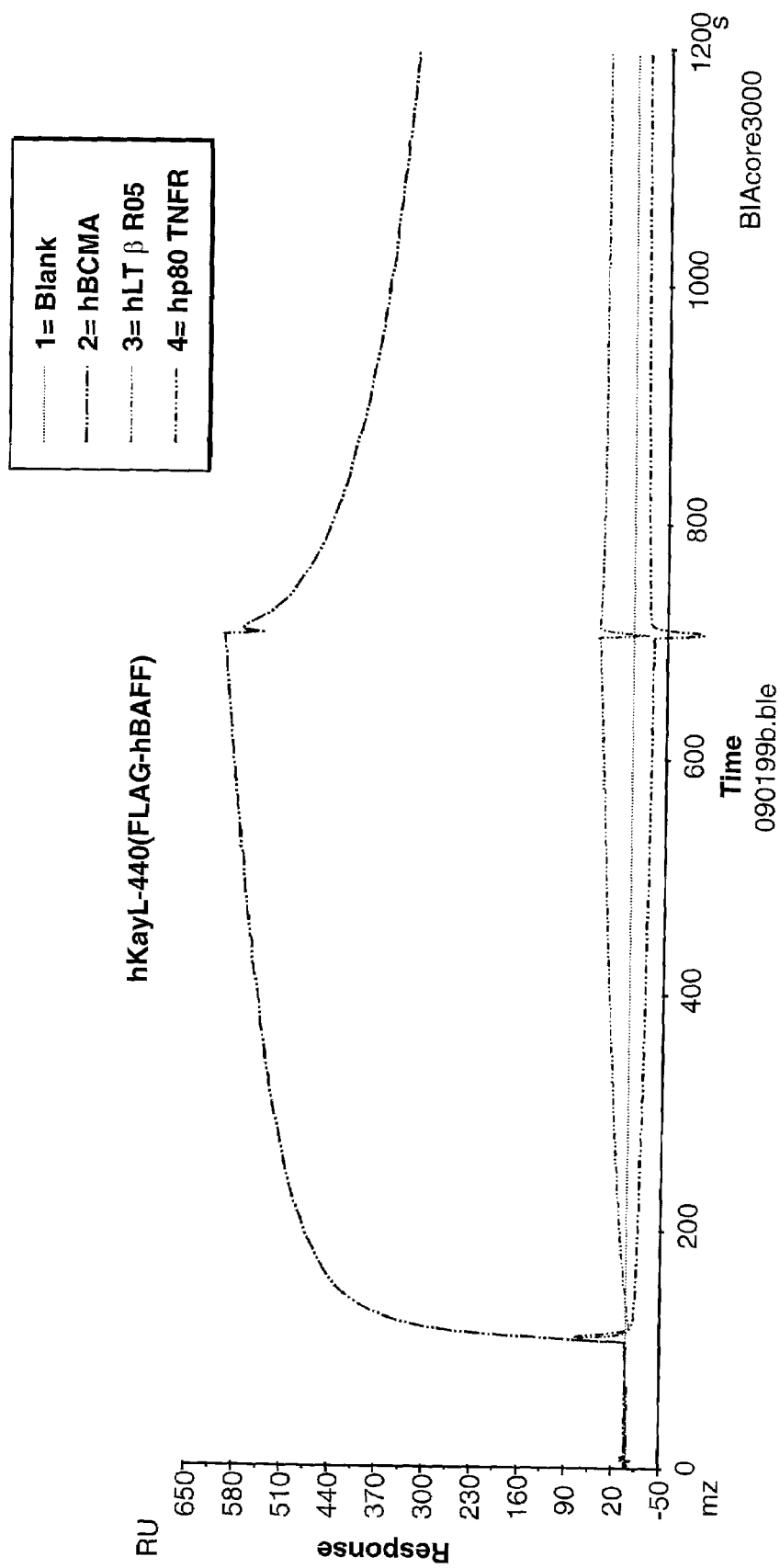
Figure 11C:
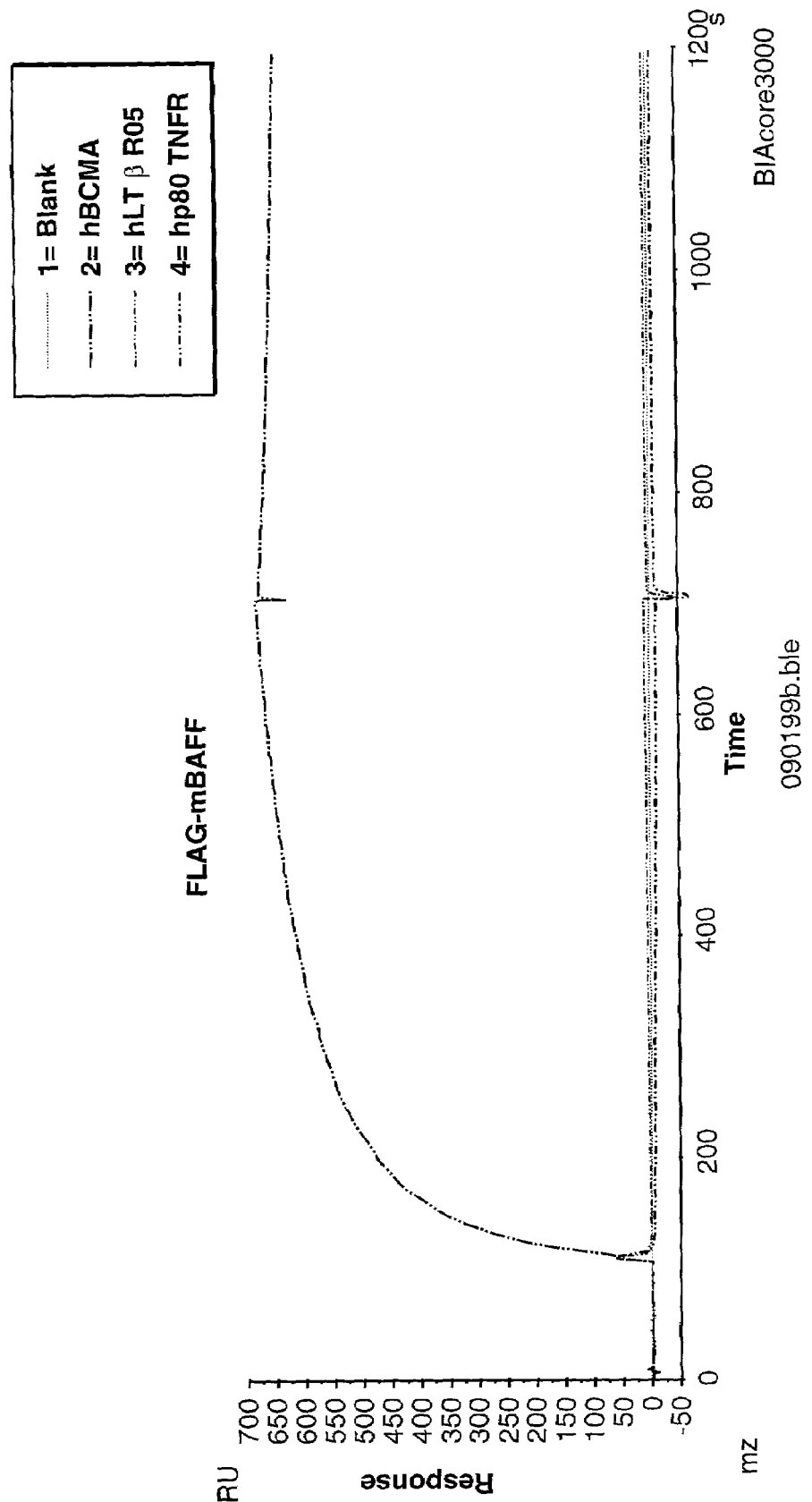

FIG. 11 shows BiaCore analysis of the binding of myc-APRIL (FIG. 11A), FLAG-hBAFF (FIG. 11B), and FLAG-mBAFF (FIG. 11C) to hBCMA, hLTbeta receptor, or hTNF-R80 or blank showing specific binding only to hBCMA.

Figure 12A:
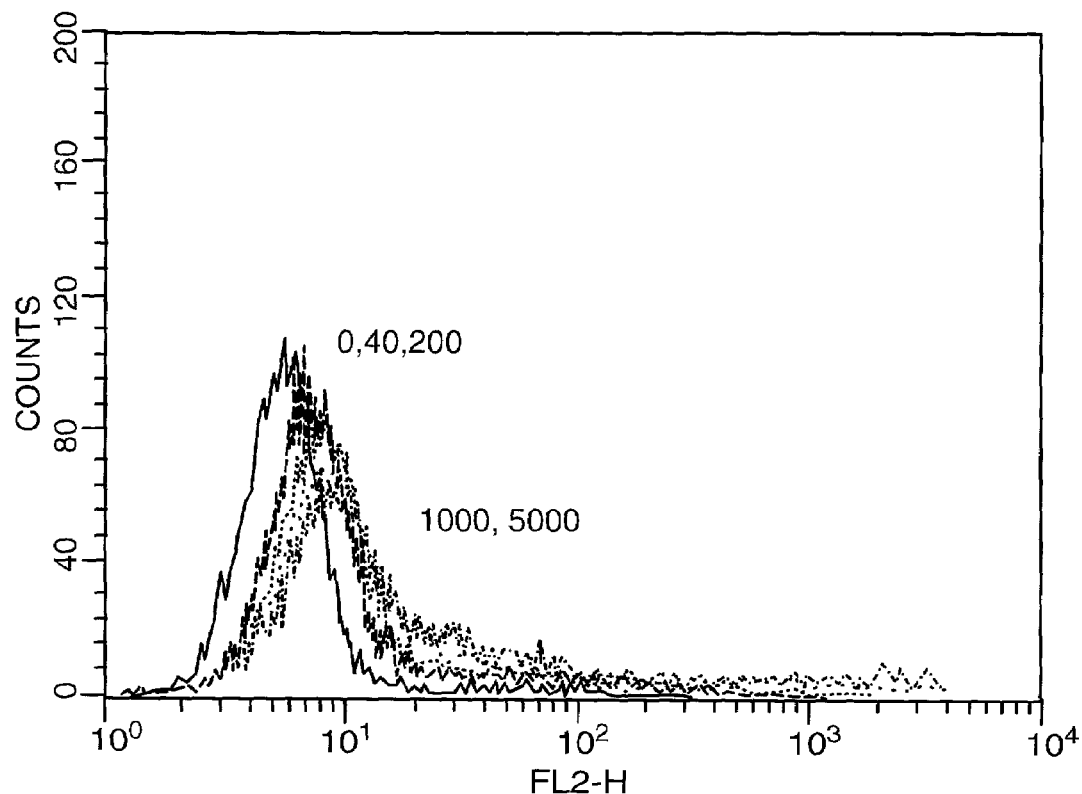
Figure 12B:
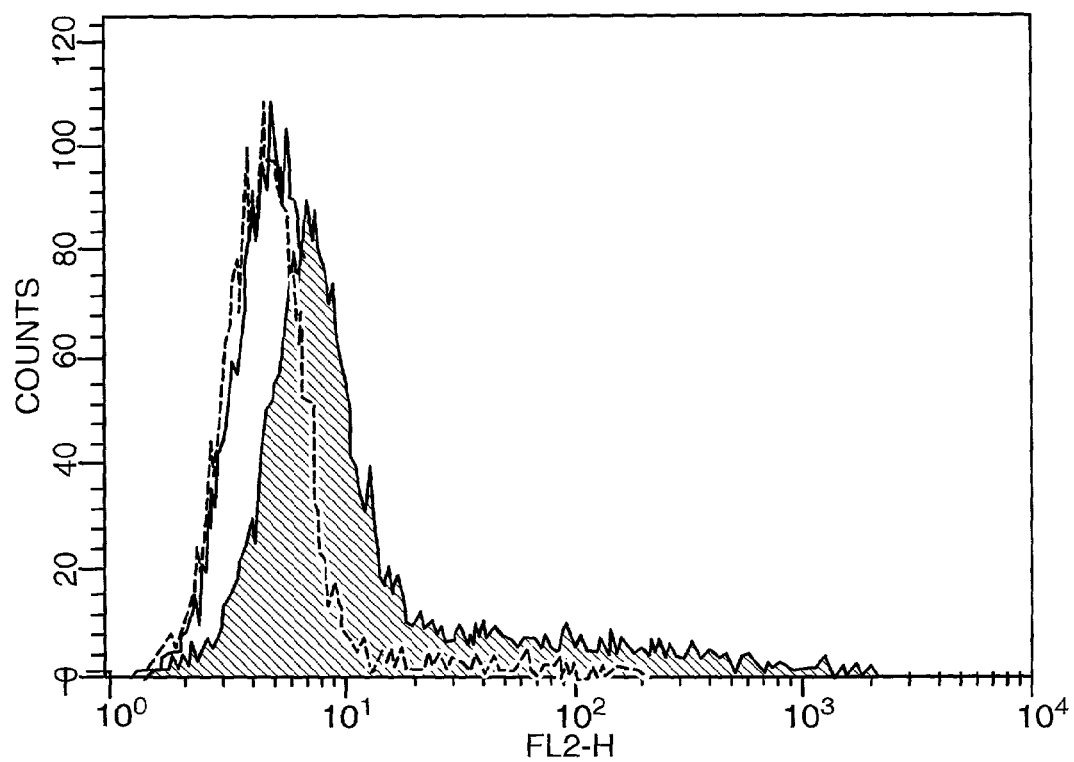

FIG. 12 shows APRIL binding to BCMA transfected cells. 293EBNA cells were transfected with a plasmid that expresses full length hBCMA. Cells were harvested 48 hours later using 5 mM EDTA and stained with myc-nAPRIL. Panel A shows that the extent of staining is dose dependent. Panel B shows that the staining decreased to background level using a soluble BCMA-Ig protein.

Figure 13:
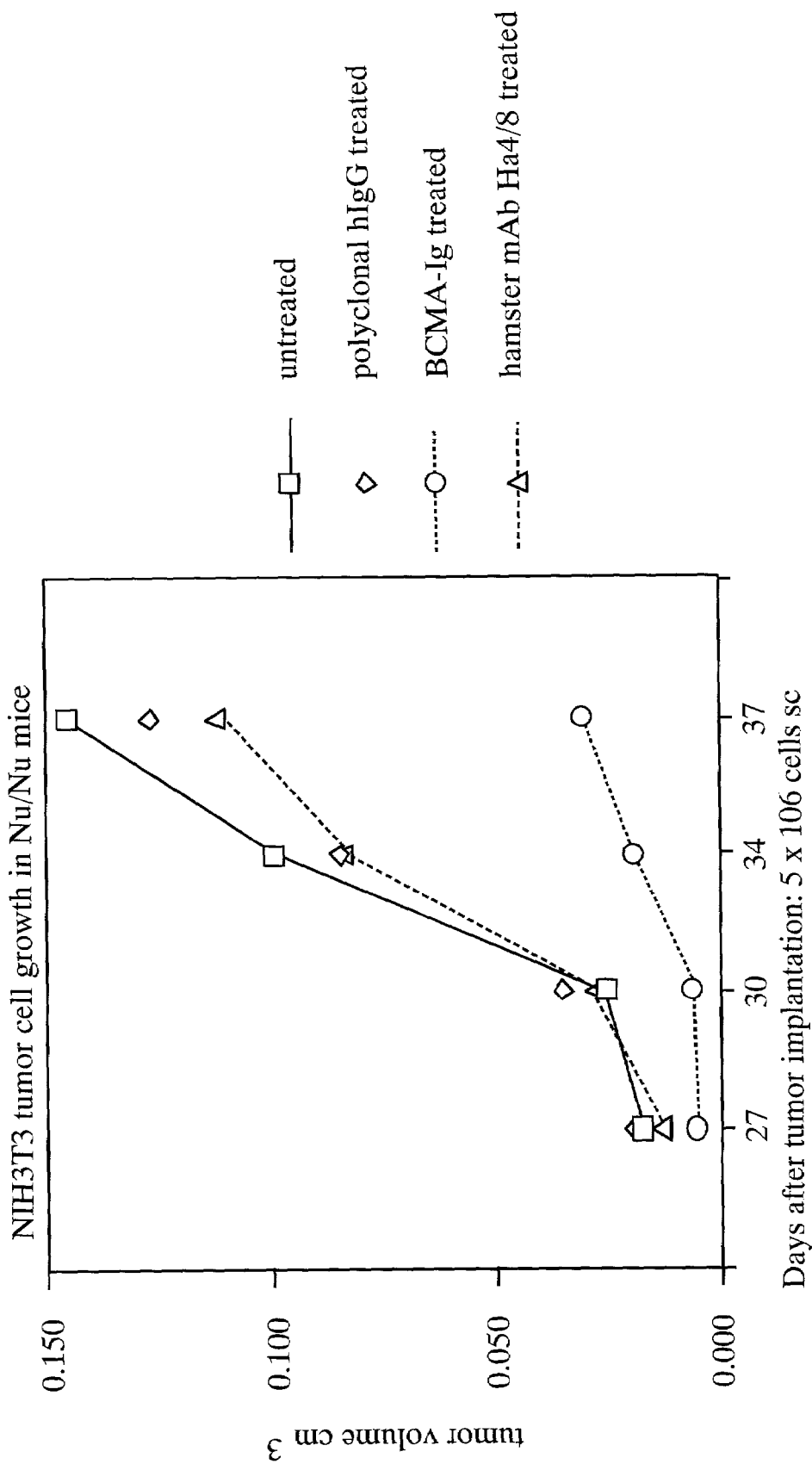

FIG. 13 shows the growth of NIH3T3 cells implanted subcutaneously in immunodeficient (Nu/Nu) mice treated with control reagents or with BCMA-Ig fusion protein. In this model the NIH3T3 cells form a fibrosarcoma.

Figure 14:
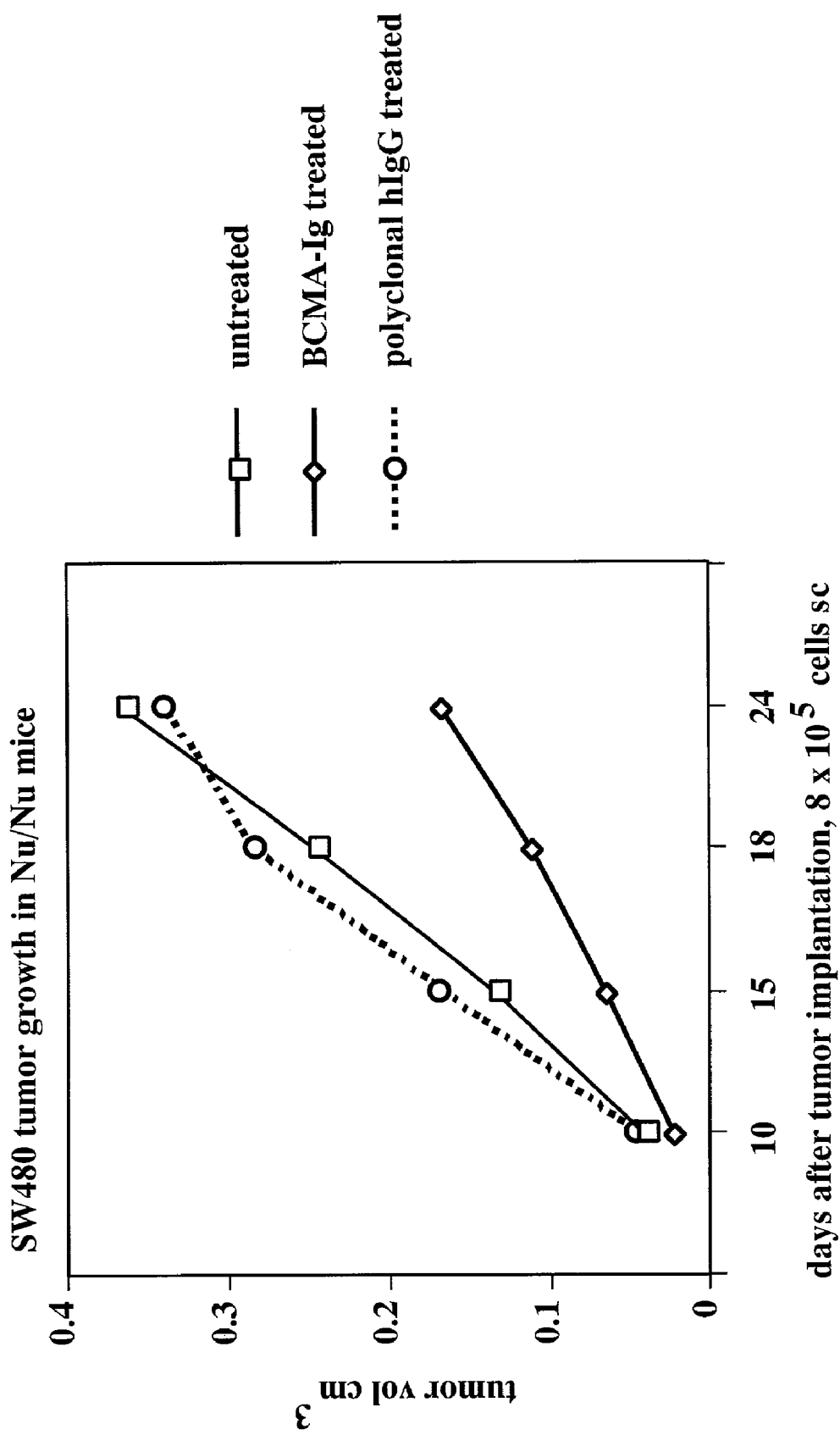

FIG. 14 shows the growth of the human colon carcinoma SW480 implanted subcutaneously in immunodeficient (Nu/Nu) mice treated with control reagents or with hBCMA-Ig fusion protein.

Figures 15, 15A:
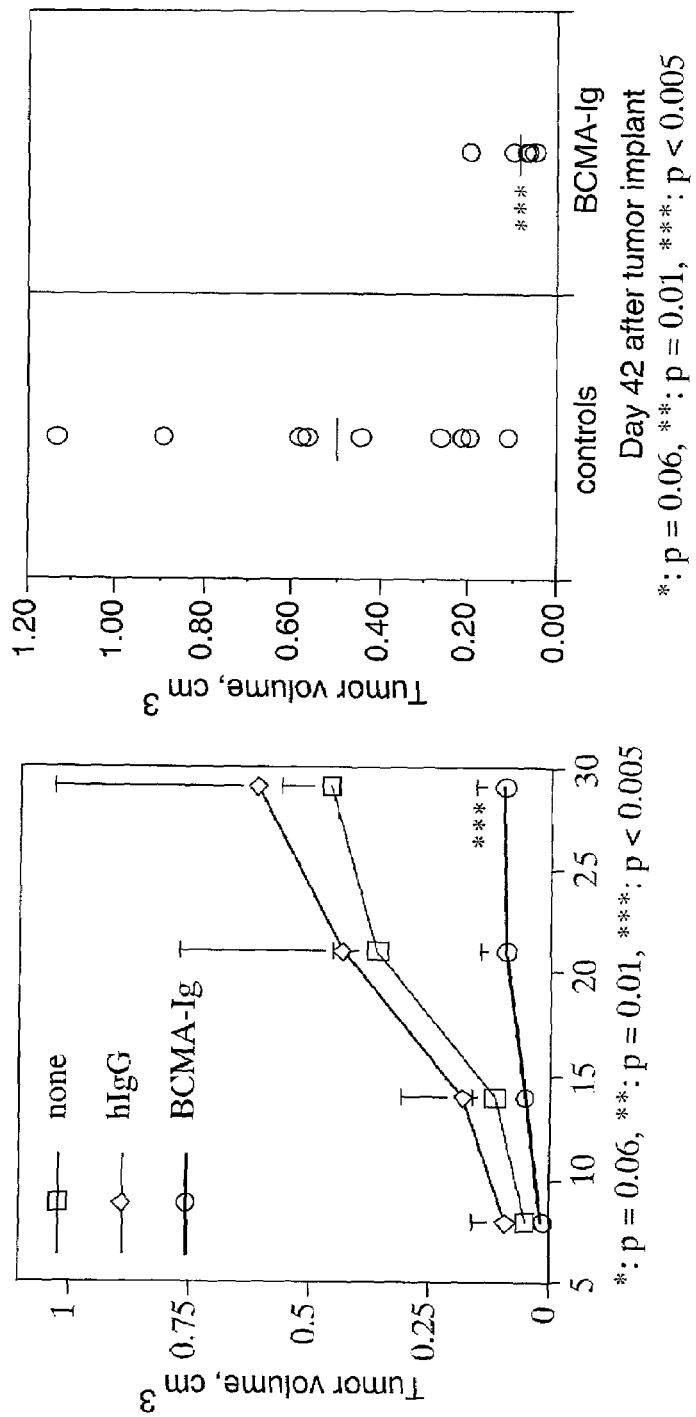
Figure 15B:
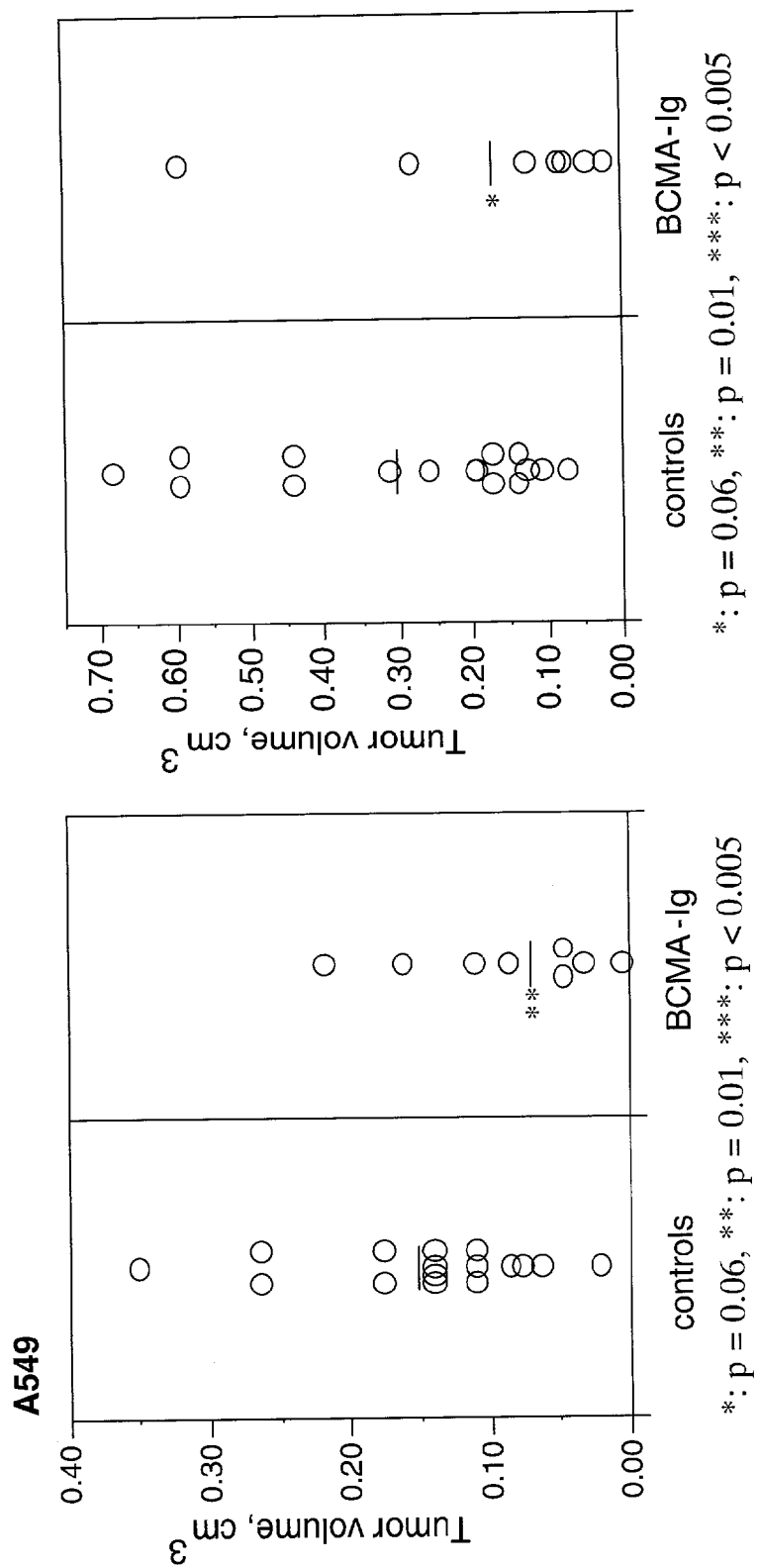

FIG. 15A shows the growth of the human colon carcinoma HT29 implanted subcutaneously in immunodeficient (Nu/Nu) mice treated with control reagents or with hBCMA-Ig fusion protein. FIG. 15B shows the growth of the human lung carcinoma A549 implanted subcutaneously in immunodeficient (Nu/Nu) mice treated with control reagents or with hBCMA-Ig fusion protein

DETAILED DESCRIPTION

Definitions

In order to more clearly and concisely point out the subject matter of the claimed invention, the following definitions are provided for specific terms used in the following written description and appended claims.

The invention will now be described with reference to the following detailed description of which the following definitions are included:

The terms "APRIL receptor" or "APRIL-R" when used herein encompass native sequence APRIL-R and APRIL-R variants. The APRIL-R may be isolated from a variety of sources, such as from murine or human tissue types or from another source, or prepared by recombinant or synthetic methods. The term APRIL-R further refers to a polypeptide which is capable of binding to the tumor necrosis family member, APRIL, or to homologs or fragments thereof. An example of an APRIL-R is BCMA.

The term "BCMA" or "BCM" refers to the novel protein for B cell maturation as described in Gras et al. (1995), International Immunology, 7: 1093-1106, "BCMAp: an integral membrane protein in the golgi apparatus of human mature B lymphocytes"; Y. Laabi et al. (1992), EMBO J., 11, 3897-3904, "A new gene BCM on Chromosome 16 is fused to the interleukin 2 gene by a t(4;16) (q26;p13) translocation in a malignant T cell lymphoma".

A "native sequence APRIL-R" comprises a polypeptide having the same amino acid sequence as APRIL-R derived from nature. Such native sequence APRIL-R can be isolated from nature or can be produced by recombinant or synthetic means. The native sequence APRIL-R can be naturally-occurring truncated or secreted forms of the APRIL-R (e.g. soluble forms containing for instance, an extracellular domain sequence), naturally-occurring variant forms (e.g., alternatively spliced forms) and naturally-occurring allelic variants of the APRIL-R. In one embodiment of the invention, the native sequence APRIL-R is a mature or full-length native sequence APRIL-R polypeptide comprising amino acids 1 to 184 of SEQ ID NO: 8 or fragment thereof.

The "APRIL-R extracellular domain" or "APRIL-R ECD" refers to a form of APRIL-R which is essentially free of transmembrane and cytoplasmic domains of APRIL-R. Ordinarily, APRIL-R extracellular domain will have less than 1% of such transmembrane and cytoplasmic domains and will preferably have less than 0.5% of such domains. Optionally, APRIL-R ECD will comprise amino acid residues 1 to 51, or 1 to 52, or 1 to 53 of SEQ ID NO: 8. In a preferred embodiment, the APRIL-ECD comprises amino acid residues 4 to 51 of SEQ ID NO: 8 or more preferably amino acid residues 8 to 41 of SEQ ID NO:8. It will be understood by the skilled artisan that the transmembrane domain identified for the APRIL-R polypeptide of the present invention is identified pursuant to criteria routinely employed in the art for identifying that type of hydrophobic domain. The exact boundaries of a transmembrane domain may vary but most likely by no more than about 5 amino acids at either end of the domain specifically mentioned herein.

"APRIL-R variant" means an active APRIL-R as defined below having at least about 80% amino acid sequence identity with the APRIL-R having the deduced amino acid sequence shown in SEQ ID NO:5 for a full-length native sequence APRIL-R or with a APRIL-R ECD sequence. Such APRIL-R variants include, for instance, APRIL-R polypeptides wherein one or more amino acid residues are added, or deleted, at the end or C-terminus of the sequence of SEQ ID NO:8. Ordinarily, a APRIL-R variant will have at least about 80% or 85% amino acid sequence identity, more preferably at least about 90% amino acid sequence identity, and even more preferably at least about 95% amino acid sequence identity with the amino acid sequence of SEQ ID NO:8.

"Percent (%) amino acid sequence identity" with respect to APRIL-R sequences identified herein is defined as the percentage of amino acid residues in a candidate sequence that are identical with the amino acid residues in the APRIL-R sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared.

The term "epitope tagged" when used herein refers to a chimeric polypeptide comprising APRIL-R, or a domain sequence thereof, fused to a "tag polypeptide". The tag polypeptide has enough residues to provide an epitope against which an antibody can be made, or which can be identified by some other agent, yet is short enough such that it does not interfere with activity of the APRIL-R. The tag polypeptide preferably also is fairly unique so that the antibody does not substantially cross-react with other epitopes. Suitable tag polypeptides generally have at least 6 amino acid residues and usually between about 8 to about 50 amino acid residues (preferably, about 10 to about 20 residues).

"Isolated" when used to describe the various polypeptides disclosed herein, means polypeptide that has been identified and separated and/or recovered from a component of its natural environment. Contaminate components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by us of a spinning cup sequenator, or (2) to homogeneity SDS-PAGE under non-reducing or reducing conditions using Coomassie blue or preferably, silver stain. Isolated polypeptide includes polypeptide in situ within recombinant cells, since at least one component of the APRIL-R's natural environment will not be present. Ordinarily, however, isolated polypeptide will be prepared by at least one purification step.

The term "antibody" is used in the broadest sense and specifically covers single APRIL-R monoclonal antibodies (including agonist, antagonist, and neutralizing antibodies) and anti-APRIL-R antibody compositions with polyepitopic specificity. The term "monoclonal antibody" as used herein refers to an antibody obtained from a population of substantially homogeneous antibodies, i.e. the individual antibodies comprising the population are identical except for possible naturally-occurring mutations that may be present in minor amounts.

A "purified preparation" or a "substantially pure preparation" of a polypeptide, as used herein, means a polypeptide that has been separated from other proteins, lipids, and nucleic acids with which it naturally occurs. Preferably, the polypeptide is also separated from other substances, e.g., antibodies, matrices, etc., which are used to purify it.

The terms, "treating", "treatment" and "therapy" as used herein refers to curative therapy, prophylactic therapy, and preventative therapy.

The terms "peptides", "proteins", and "polypeptides" are used interchangeably herein.

"Biologically active" as used herein, means having an in vivo or in vitro activity which may be performed directly or indirectly. Biologically active fragments of APRIL-R may have, for example, 70% amino acid homology with the active site of the receptor, more preferably at least 80%, and most preferably, at least 90% homology. Identity or homology with respect to the receptor is defined herein as the percentage of amino acid residues in the candidate sequence which are identical to the APRIL-R residues in SEQ ID NO:8.

The term "mammal" as used herein refers to any animal classified as a mammal including humans, cows, horses, dogs, mice and cats. In preferred embodiment of the invention, the mammal is a human.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature.

Reference will now be made in detail to the present preferred embodiments of the invention. This invention relates to the use of APRIL-R and APRIL-R related molecules to effect the growth and maturation of B-cells and non-B cells, specifically as they relate to tumor cells. The invention also relates to the use of APRIL-R and APRIL-R related molecules to effect responses of the immune system, as necessitated by immune-related disorders. Additionally, this invention encompasses the treatment of cancer and immune disorders through the use of a APRIL-R, or APRIL-R related gene through gene therapy methods.

The APRIL-R and homologs thereof produced by hosts transformed with the sequences of the invention, as well as native APRIL-R purified by the processes known in the art, or produced from known amino acid sequences, are useful in a variety of methods for anticancer, antitumor and immunoregulatory applications. They are also useful in therapy and methods directed to other diseases.

Another aspect of the invention relates to the use of the polypeptide encoded by the isolated nucleic acid encoding the APRIL-R in "antisense" therapy. As used herein, "antisense" therapy refers to administration or in situ generation of oligonucleotides or their derivatives which specifically hybridize under cellular conditions with the cellular mRNA and/or DNA encoding the ligand of interest, so as to inhibit expression of the encoded protein, i.e. by inhibiting transcription and/or translation. The binding may be by conventional base pair complementarity, or, for example, in the case of binding to DNA duplexes, through specific interactions in the major groove of the double helix. In general, "antisense" therapy refers to a range of techniques generally employed in the art, and includes any therapy which relies on specific binding to oligonucleotide sequences.

An antisense construct of the present invention can be delivered, for example, as an expression plasmid, which, when transcribed in the cell, produces RNA which is complementary to at least a portion of the cellular mRNA which encodes Kay-ligand. Alternatively, the antisense construct can be an oligonucleotide probe which is generated ex vivo. Such oligonucleotide probes are preferably modified oligonucleotides which are resistant to endogenous nucleases, and are therefore stable in vivo. Exemplary nucleic acids molecules for use as antisense oligonucleotides are phosphoramidates, phosphothioate and methylphosphonate analogs of DNA (See, e.g., U.S. Pat. Nos. 5,176,996; 5,264,564; and 5,256,775). Additionally, general approaches to constructing oligomers useful in antisense therapy have been reviewed, for example, by Van Der Krol et al., (1988) Biotechniques 6:958-976; and Stein et al. (1988) Cancer Res 48: 2659-2668, specifically incorporated herein by reference.

The APRIL-R of the invention, as discussed above, is a member of the TNF receptor family. The protein, fragments or homologs thereof may have wide therapeutic and diagnostic applications.

The polypeptides of the invention specifically interact with APRIL, a polypeptide previously described in WO99/12964 incorporated by reference herein. However, the peptides and methods disclosed herein enable the identification of molecules which specifically interact with the APRIL-R or fragments thereof.

The claimed invention in certain embodiments includes methods of using peptides derived from APRIL-R which have the ability to bind to APRIL. Fragments of the APRIL-R's can be produced in several ways, e.g., recombinantly, by PCR, proteolytic digestion or by chemical synthesis. Internal or terminal fragments of a polypeptide can be generated by removing one or more nucleotides from one end or both ends of a nucleic acid which encodes the polypeptide. Expression of the mutagenized DNA produces polypeptide fragments.

Polypeptide fragments can also be chemically synthesized using techniques known in the art such as conventional Merrifield solid phase f-moc or t-boc chemistry. For example, peptides and DNA sequences of the present invention may be arbitrarily divided into fragments of desired length with no overlap of the fragment, or divided into overlapping fragments of a desired length. Methods such as these are described in more detail below.

Generation of Soluble Forms of APRIL-R

Soluble forms of the APRIL-R can often signal effectively and hence can be administered as a drug which now mimics the natural membrane form. It is possible that the APRIL-R claimed herein are naturally secreted as soluble cytokines, however, if not, one can reengineer the gene to force secretion. To create a soluble secreted form of APRIL-R, one would remove at the DNA level the N-terminus transmembrane regions, and some portion of the stalk region, and replace them with a type I leader or alternatively a type II leader sequence that will allow efficient proteolytic cleavage in the chosen expression system. A skilled artisan could vary the amount of the stalk region retained in the secretion expression construct to optimize both ligand binding properties and secretion efficiency. For example, the constructs containing all possible stalk lengths, i.e. N-terminal truncations, could be prepared such that proteins starting at amino acids 1 to 52 would result. The optimal length stalk sequence would result from this type of analysis.

Generation of Antibodies Reactive with the APRIL-R

The invention also includes antibodies specifically reactive with the claimed APRIL-R or its co-receptors. Anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide. Techniques for conferring immunogenicity on a protein or peptide include conjugation to carriers, or other techniques, well known in the art.

An immunogenic portion of APRIL-R or its co-receptors can be administered in the presence of an adjuvant. The progress of immunization can be monitored by detection of antibody titers in plasma or serum. Standard ELISA or other immunoassays can be used with the immunogen as antigen to assess the levels of antibodies.

In a preferred embodiment, the subject antibodies are immunospecific for antigenic determinants of APRIL-R or its co-receptors, e.g. antigenic determinants of a polypeptide of SEQ ID NO:8, or a closely related human or non-human mammalian homolog (e.g. 70, 80 or 90 percent homologous, more preferably at least 95 percent homologous). In yet a further preferred embodiment of the present invention, the anti-APRIL-R or anti-APRIL-co-receptor antibodies do not substantially cross react (i.e. react specifically) with a protein which is e.g., less than 80 percent homologous to SEQ ID NO:8; preferably less than 90 percent homologous with SEQ ID NO:8; and, most preferably less than 95 percent homologous with SEQ ID NO:8. By "not substantially cross react", it is meant that the antibody has a binding affinity for a non-homologous protein which is less than 10 percent, more preferably less than 5 percent, and even more preferably less than 1 percent, of the binding affinity for a protein of SEQ ID NO.8.

The term antibody as used herein is intended to include fragments thereof which are also specifically reactive with APRIL-R, or its receptors. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibodies of the present invention are further intended to include biospecific and chimeric molecules having anti-APRIL-R or anti-APRIL-co-receptor activity. Thus, both monoclonal and polyclonal antibodies (Ab) directed against APRIL-R, and their co-receptors, and antibody fragments such as Fab' and F(ab')$_2$, can be used to block the action of the APRIL-R and its respective co-receptors.

Various forms of antibodies can also be made using standard recombinant DNA techniques. (Winter and Milstein, Nature 349: 293-299 (1991) specifically incorporated by reference herein.) For example, chimeric antibodies can be constructed in which the antigen binding domain from an animal antibody is linked to a human constant domain (e.g. Cabilly et al., U.S. Pat. No. 4,816,567, incorporated herein by reference). Chimeric antibodies may reduce the observed immunogenic responses elicited by animal antibodies when used in human clinical treatments.

In addition, recombinant "humanized antibodies" which recognize APRIL-R or its co-receptors can be synthesized. Humanized antibodies are chimeras comprising mostly human IgG sequences into which the regions responsible for specific antigen-binding have been inserted. Animals are immunized with the desired antigen, the corresponding antibodies are isolated, and the portion of the variable region sequences responsible for specific antigen binding are removed. The animal-derived antigen binding regions are then cloned into the appropriate position of human antibody genes in which the antigen binding regions have been deleted. Humanized antibodies minimize the use of heterologous (i.e. inter species) sequences in human antibodies, and thus are less likely to elicit immune responses in the treated subject.

Construction of different classes of recombinant antibodies can also be accomplished by making chimeric or humanized antibodies comprising variable domains and human constant domains (CH1, CH2, CH3) isolated from different classes of immunoglobulins. For example, antibodies with increased antigen binding site valencies can be recombinantly produced by cloning the antigen binding site into vectors carrying the human: chain constant regions. (Arulanandam et al., J. Exp. Med., 177: 1439-1450 (1993), incorporated herein by reference.)

In addition, standard recombinant DNA techniques can be used to alter the binding affinities of recombinant antibodies with their antigens by altering amino acid residues in the vicinity of the antigen binding sites. The antigen binding affinity of a humanized antibody can be increased by mutagenesis based on molecular modeling. (Queen et al., Proc. Natl. Acad. Sci. 86: 10029-33 (1989)) incorporated herein by reference.

Generation of Analogs: Production of Altered DNA and Peptide Sequences

Analogs of the APRIL-R can differ from the naturally occurring APRIL-R in amino acid sequence, or in ways that do not involve sequence, or both. Non-sequence modifications include in vivo or in vitro chemical derivatization of the APRIL-R. Non-sequence modifications include, but are not limited to, changes in acetylation, methylation, phosphorylation, carboxylation or glycosylation.

Preferred analogs include APRIL-R biologically active fragments thereof, whose sequences differ from the sequence given in SEQ ID NO:8, by one or more conservative amino acid substitutions, or by one or more non-conservative amino acid substitutions, deletions or insertions which do not abolish the activity of APRIL-ligand. Conservative substitutions typically include the substitution of one amino acid for another with similar characteristics, e.g. substitutions within the following groups: valine, glycine; glycine, alanine; valine, isoleucine, leucine; aspartic acid, glutamic acid; asparagine, glutamine; serine, threonine; lysine, arginine; and, phenylalanine, tyrosine.

Uses

The full length APRIL-R gene (SEQ ID NO:8) or portions thereof may be used as hybridization probes for a cDNA library to isolate, for instance, still other genes which have a desired sequence identity to the APRIL-R sequence disclosed in SEQ ID NO: 6. Nucleotide sequences encoding APRIL-R can also be used to construct hybridization probes for mapping the gene which encodes the APRIL-R and for the genetic analysis of individuals with genetic disorders. Screening assays can be designed to find lead compounds that mimic the biological activity of a APRIL-R. Such screening assays will include assays amenable to high-throughput screening of chemical libraries, making them particularly suitable for identifying small molecule drug candidates. Small molecules contemplated include synthetic organic or inorganic compounds. Nucleic acids which encode APRIL-R or its modified forms can also be used to generate either transgenic animals or "knock out" animals which in turn are useful in the development and screening of therapeutically useful reagents, including for example cancer reagents.

The APRIL-R and homologs thereof produced by hosts transformed with the sequences of the invention, as well as native APRIL-R purified by the processes known in the art, or produced from known amino acid sequences, are useful in a variety of methods for anticancer applications.

In one embodiment of the invention is a method of treating a mammal for a condition associated with undesired cell proliferation by administering to the mammal a therapeutically effective amount of a composition comprising an APRIL-R antagonist, wherein the APRIL-R antagonist comprises a polypeptide that antagonizes the interaction between APRIL and its cognate receptor or receptors, with a pharmaceutically acceptable recipient.

In a preferred embodiment the cognate receptor of APRIL on the surface of the cell is BCMA.

The method can be used with any APRIL-R antagonist that has a polypeptide that antagonizes the interaction between APRIL and its cognate receptor or receptors. Examples of APRIL-R antagonists include but are not limited to soluble APRIL-R polypeptide, including but not limited to soluble BCMA; soluble chimeric APRIL-R molecules, including but not limited to BCMA-IgG-Fc and anti-APRIL-R antibody homologs, including but not limited to anti-BCMA monoclonal antibody.

The method of the invention can be used with any condition associated with undesired cell proliferation. In particular the methods of the present invention can be used to treat tumor cells which express APRIL and/or APRIL-R (i.e. BCMA).

Examples of cancers whose cell proliferation is modulated by APRIL may be screened by measuring in vitro the level of APRIL and/or APRIL-R (i.e. BCMA) message expressed in tumor tissue libraries. Tumor tissue libraries in which APRIL and/or APRIL-R (i.e. BCMA) message is highly expressed would be candidates. Alternatively, one may screen for candidates searching the public and private databases (i.e. Incyte data base) with, for example, the full length human APRIL cDNA sequence. Applying these techniques, it was found, for example, that APRIL mRNA expression was detected in a large number of tumor types, including but not limited to those found in Table 1 below:

TABLE 1

Library Description

Prostate tumor line, LNCaP, CA, 50M, untreated, TIGR
T-lymphocyte tumor, lymphoma, TIGR
Ovary tumor, papillary serous cystadenoCA
Lung, mw/adenoCA, COPD, 47M
Breast tumor, adenoCA, 46F, SUB, m/BRSTNOT33
Ganglion, dorsal root, cervical, aw/lymphoma, 32M, NORM
Brain tumor, frontal, neuronal neoplasm, 32M
Prostate tumor, adenoCA, 59M, SUB, m/PROSNOST19
Colon tumor, hepatic flexure, adenoCA, 55M, SUB, m/COLATMT01
Pancreatic tumor, TIGR
Paraganglion tumor, paraganglioma, aw/renal cell CA, 46M
Breast, mw/ductal CA, 43F, m/BRSTTUT16
Kidney tumor, renal cell CA, 51F
Bladder, mw/TC CA, CA in situ, 60M, m/BLADTUT04
Uterus tumor, endometrial, F, TIGR
Prostate, BPH, mw/adenoCA, PIN, 59M
Lung, mw/adenoCA, 53M, m/LUNGTUT17
Bone tumor/line, MG-63, osteoSAR/giant cell, M/F, pool, RP
Brain, frontal cortex, aw/lung CA, 77M
Colon tumor, adenoCA, NORM, SUB, CGAP
Lung tumor, squamous cell CA, 57M
Lung, mw/adenoCA, 63M
Prostate, AH, mw/adenoCA, 50M, m/PROSTUT01
Periph blood, B-lymphocytes, CLL, pool, NORM, 3' CGAP
Colon tumor, adenoCA, pool, NORM, 3'/5' CGAP
Kidney, mw/renal cell CA, 8,53F, pool, NORM
Ovary, dermoid cyst, 22F
Colon tumor, adenoCA, NORM, 3' CGAP
Colon tumor, adenoCA, 3', CGAP
Prostate, BPH, mw/adenoCA, 70M, SUB
Ovary tumor, mets colon adenoCA, 58F
Uterus, myometrium, mw/leiomyoma, 43F
Sm intestine, ileum, mw/CUC, 25F
Lymph node, peripancreatic, aw/pancreatic adenoCA, 65M
Ovary, aw/leiomyomata, 36F, NORM
Lung, mw/spindle cell carcinoid, 62F
Lung tumor, squamous CA, 50M
Brain tumor, meningioma, 36M
Tumor, adenoCA, 65F, m/PANCNOT08
Lung, mw/endobronchial carcinoid, 33M
Adrenal gland, mw/pheochromocytoma, 43F, m/ADRETUT07
Brain tumor, frontal, meningioma, 50M
Kidney tumor, clear cell type cancer, pool, NORM, 3' CGAP
Breast, mw/lobular CA, 67F
Lung, mw/mets osteoSAR, aw/pleura mets, 58M, NORM
Prostate tumor, adenoCA, 59M, SUB, m/PROSNOT19
Sm intestine tumor, ileum, mets endometrial adenoCA, 64F
Ovary tumor, adenoCA, 58F
Breast, NF breast disease, 46F
Brain tumor, frontal, mets hypernephroma, 58M
Kidney tumor, Wilms', pool, WM/WN
Lung, mw/mets thyroid CA, 79M, m/LUNGTUT02
Lung tumor, mets thyroid CA, 79M, m/LUNGNOT03
Parathyroid tumor, adenoma, M/F, NORM, WM
Pancreatic tumor, anaplastic CA, 45F
Ovary, mw/mucinous cystadenoCA, 43F, m/OVARTUT01
Lung tumor, squamous cell CA, pooled, NORM, CGAP
Breast tumor, adenoCA, 46F, m/BRSTNOT17
Uterus, mw/leiomyoma, aw/colon adenoCA, 45F
Lung, mw/adenoCA, aw/node, diaphragm mets, 63F
Breast tumor, adenoCA, 46F, m/BRSTNOT33
Prostate, adenoCA, 66M, m/PROSNOT15, PROSDIN01
Breast tumor, adenoCA, 54F, m/BRSTNOT03
Germ cell tumor, pool, SUB, 3' CGAP
Bone marrow, tibia, aw/mets alveolar rhabdomyoSAR, 16M
Prostate, AH, mw/adenoCA, 57M, m/PROSTUT04
Breast, PF changes, mw/adenoCA, 55F, m/BRSTTUT01
Uterus tumor, serous papillary CA, F, pooled, 3' CGAP
Ovary tumor, mucinous cystadenoCA, 43F, m/OVARNOT03
Breast, PF changes, mw/adenoCA, intraductal CA, 43F
Breast, mw/ductal CA, CA in situ, aw/node mets, 62F
Neuroganglion tumor, ganglioneuroma, 9M
Pancreas tumor, adenoCA, 3' CGAP
Uterus tumor, endometrial adenoCA, F, pooled, 3' CGAP
Lung tumor, neuroendocrine carcinoma, pool, NORM, 3' CGAP The APRIL-R antagonists of the subject invention which are used in treating conditions associated with undesired cell proliferation, in particular tumor therapy, advantageously inhibit tumor cell growth greater than 10%, 20%, 30% or 40% and most advantageously greater than 50%. The APRIL-R antagonists are obtained through screening (see, for example, the discussion in Example 6). For example, APRIL-R antagonists can be selected on the basis of growth inhibiting activity (i.e. greater than 10%, 20%, 30%, 40% or 50%) against the human colon carcinoma HT29 or human lung carcinoma A549 (see, for example, the discussion in FIG. 15) which are derived from a colon and lung tumor respectively.

Another embodiment of the invention, provides methods of inhibiting B-cell and non-B cell growth, dendritic cell-induced B-cell growth and maturation or immunoglobulin production in an animal using APRIL-R polypeptide.

In another embodiment, the invention provides methods of using APRIL-R in the treatment of autoimmune diseases, hypertension, cardiovascular disorders, renal disorders, B-cell lympho-proliferate disorders, immunosuppressive diseases, organ transplantation, inflammation, and HIV. Also included are methods of using agents for treating, suppressing or altering an immune response involving a signaling pathway between APRIL-R and its ligand.

The present invention also provides pharmaceutical compositions comprising a APRIL-R polypeptide and a pharmaceutically acceptable excipient. Suitable carriers for a APRIL-R polypeptide, for instance, and their formulations, are described in *Remington' Pharmaceutical Sciences*, 16$^{th}$ ed., 1980, Mack Publishing Co., edited by Oslo et al. Typically an appropriate amount of a pharmaceutically acceptable salt is used in the formulation to render the formulation isotonic. Examples of the carrier include buffers such as saline, Ringer's solution and dextrose solution. The pH of the solution is preferably from about 5 to about 8, and more preferably from about 7.4 to about 7.8. Further carriers include sustained release preparations such as semipermeable matrices of solid hydrophobic polymers, which matrices are in the form of shaped articles, e.g. liposomes, films or microparticles. It will be apparent to those of skill in the art that certain carriers may be more preferable depending upon for instance the route of administration and concentration of the a APRIL-R polypeptide being administered.

Administration may be accomplished by injection (e.g., intravenous, intraperitoneal, subcutaneous, intramuscular) or by other methods such as infusion that ensure delivery to the bloodstream in an effective form.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, Molecular Cloning: A Laboratory Manual, 2nd edition. (Sambrook, Fritsch and Maniatis, eds.), Cold Spring Harbor Laboratory Press, 1989; DNA Cloning, Volumes I and II (D. N. Glover, ed), 1985; Oligonucleotide Synthesis, (M. J. Gait, ed.), 1984; U.S. Pat. No. 4,683,195 (Mullis et al.,); Nucleic Acid Hybridization (B. D. Hames and S. J. Higgins, eds.), 1984; Transcription and Translation (B. D. Hames and S. J. Higgins, eds.), 1984; Culture of Animal Cells (R. I. Freshney, ed). Alan R. Liss, Inc., 1987; Immobilized Cells and Enzymes, IRL Press, 1986; A Practical Guide to Molecular Cloning (B. Perbal), 1984; Methods in Enzymology, Volumes 154 and 155 (Wu et al., eds), Academic Press, New York; Gene Transfer Vectors for Mammalian Cells (J. H. Miller and M. P. Calos, eds.), 1987, Cold Spring Harbor Laboratory; Immunochemical Methods in Cell and Molecular Biology (Mayer and Walker, eds.), Academic Press, London, 1987; Handbook of Experiment Immunology, Volumes I-IV (D. M. Weir and C. C. Blackwell, eds.), 1986; Manipulating the Mouse Embryo, Cold Spring Harbor Laboratory Press, 1986.

The following Examples are provided to illustrate the present invention, and should not be construed as limiting thereof.

EXAMPLES

The following methods were used in the Examples disclosed hereinafter.

Methods:

Cloning and Expression of Myc-Tagged Murine APRIL (CCM776) in *Pichia pastoris*.

The expression vector pCCM213.10 was constructed by taking PDR004 (H98 muAPRIL with superFAS-ligand stalk attached to N terminus along with FLAG epitope tag) and excising out the mu APRIL coding sequence from Sac I to Not1. Synthetic oligonucleotides LTB-559 and 560 form a Xho-1-Sac1 linker which contain an alpha mating factor leader sequence, myc epitope tag, as well as the KEL motif from FAS ligand. Both the muAPRIL fragment and linker were ligated into the Xho-1-Not1 sites of pccm211, a *Pichia pastoris* expression plasmid.

PCCM213.10 was linearized with Stu 1, electroporated into GS115 strain (his4-) and plated into minimal media containing dextrose. HIS4 transformants were analyzed for protein expression by inoculating a single representative colony in rich meida (BMGY: Buffered glycerol complex medium) and allowing it to grow to density for 48 hours at 30C. Cultures were spun, and cell pellets were resuspended (1:5) in a rich induction media containing 1.5% methanol (BMMY:Buffered methanol complex media). After two days of induction at 30C, supernatants were run out on SDS-PAGE and assessed for the presence of muAPRIL. Coomassie staining and Western blot (with the anti-myc mAb 9E10) showed that one strain, CCM776, produced adequate amounts of the glycosylated form myc-tagged-H98 muAPRIL protein.

Myc-mAPRIL Purification

Myc-mApril, a protein of 149 amino acids was expressed in *pichia*. This protein has an isoelectric point of 7.45. 175 ml of *pichia* supernatant was dialyzed and buffer exchanged to 10 mM Tris pH 6.8 overnight and then passed through a 20 ml SP column. The column was washed extensively with 10 mM Tris-HCl, pH 6.8, and eluted with 250 n mM NaCl in PBS. A second step purification was achieved using a gel filtration column (S300). Fractions containing myc-April from 20 ml SP column were concentrated by centrifugation to a volume of 7 ml. After gel filtration, we recovered 8 mg of myc-APRIL as detected by OD and coomassie gel. We also performed Western blot analysis using mouse monoclonal 9E10 antibody (anti-myc) showing that the myc tag is intact after the purification steps. N terminal sequence verified that the purified protein corresponds to myc-mApril.

FLAG-Human April Purification.

Plasmid ps429 (subsequently named p1448) was used to transiently transfect 293 T cells using lipofectamine reagent (Gibco-Brl) and serum free media. The plasmid, constructed in the mammalian expression vector PCR3 (Invitrogen) encodes the receptor-binding domain of human APRIL, with an N-terminal protein into the cell culture media. FLAG-APRIL protein was purified from serum free media using an anti-FLAG mAb M2 column and excess purified FLAG peptide, following the manufacturers' instructions (Kodak).

HBMCA-Fc Purification.

HBMCA-Fc was transiently tranfected into 293 cells. Conditioned media from 293 cells over-expressing hBCM-Fc was loaded into a protein A column. Protein was eluted using 25 mM phosphate 100 nM NaCl pH 2.8 followed by neutralization with ½₀ volume of 0.5 M NaPO4 pH 8.6. Selected fractions based in OD 280 were subject to reducing and non-reducing SDS-PAGE gels and western blots to identify the purified protein. 3 mg of protein were recovered from 500 ml of conditioned media.

Myc-mAPRIL Binds to Various Cell Lines in FACS Analysis.

450 ng/ml of purified myc-mAPRIL was bound to cell lines in 100 ul PBS/2% FBS+Fc blocking reagents (FcBlock@ 20 ug/ml (Pharmingen) and purified human IgG@ 10 ug/ml (Sandoz) on ice for 1 hour. Positive binding was revealed using specific rabbit anti-murine APRIL antisera (1:500) and donkey anti-rabbit IgG-FITC (Jackson). Cell lines A20, Raji, NIH3T3, and HT29 were maintained in media as suggested by the supplier (ATCC Bethesda, Md.). BJAB cells were cultured in HEPES-buffered RPMI supplemented with 10% FBS and L-glutamine. In competition assays 450 ng/ml myc-murine APRIL was added with 1 ug/ml of competitor protein.

Example 1

Detection of APRIL Binding to APRIL-R Using a Plate Assay

In this example, BCMA Association with April was tested.

In order to test whether BCMA associates with April we performed a co-immunoprecipitation experiment. Both soluble proteins hBCMA-Fc and myc-mApril were used in this experiment.

HBCMA-Fc and LTbR-Fc were added with different TNF ligands: myc-mApril; myc-CD40L and myc-RANKL into media containing 10% FBS for ½ hour at room temperature. Fc proteins were bound to protein A beads for 1-2 hours, washed three times with 1 ml of PBS, analyzed by immunoblotting with mouse monoclonal 9E10 (anti-myc) antibody and developed using enhanced chemiluminescence.

We detected myc-APRIL in hBCMA-Fc immunoprecipitates indicating that BCMA interacts with April in a specific way since other TNF ligands, myc-CD40L and myc-RANKL did not have the ability to bind to BCMA. Myc-April does not associate with LTbR-Fc.

The same membrane was stripped and reblotted with anti-hIG-HRP to show that the same amount of LTbR-Fc with BCMA-Fc were used in the immunoprecipates.

Example 2 hBCMA Binds to Flag-hAPRIL

This example describes that hBCMA-FC interacts with FLAG-hAPRIL.

ELISA analysis: Coated plates with receptor-Fc fusion proteins (hBCMA-Fc-739 or hTNFR2-Fc-492) at 1 ug/ml in carbonate pH 9.6, overnight, 4C. Blocked for 2 hours at room temperature using PBS/5% non fat dry milk/05% Tween-20. 2× serial dilution of ligands were made in 100 ul of blocking buffer (TNFa-197 from 1000 ng/ml, muBAFF-657 from 1000 ng/ml, hApril-507 from 2000 ng/ml (inactive), hApril-429 from 5× concentrated media). After incubation with ligands the plate was washed in PBS) 0.5% Tween-20 and probed with 0.5 ug/ml anti-FLAG mAb M2 in dilution buffer. The antibody was then detected using anti-mouse-PO ½₀₀₀ with enzymatic development (OPD).

Immunoprecipitation experiments: 293T cells were transfected with indicated expression plasmid (Rec-Fc or flag ligand) in 9 cm plate. Transfected cells were left for 5d in 8 ml Optimem media (Gibco-BRL). Immunoprecipitation were performed by mixing 200 ul of each receptor-conditioned media with 200 ul of each ligand-conditioned media+ 400 ul PBS+10 ul ProtG-Sepharose. These were rotated 1 h on a wheel, washed 4× with 1 ml PBS, then boiled in 50 ul sample buffer (+DTT). 20 ul of each immunoprecipitation was loaded per lane. Reveal blotting was done with 1 ug/ml anti-FLAG M2 mAb (Sigma, St Louis Mo.) and anti-mouse PO (½₀₀₀). A reprobe blot with anti-human-PO was also checked: 100 ul conditioned media was precipitated with MeOH/CHC13/lysozyme. This mix was boiled in 50 ul sample buffer (+DTT) and 20 ul was loaded. A Reveal blot was performed with anti-FLAG mAb M2 (1 ug/ml) and anti-mouse-PO (½₀₀₀).

Example 3

BiaCore Analysis

This example describes the binding of myc-mAPRIL; hKayL-440 (hBAFF); and Flag-mBAFF to hBCMA-Ig, hLT-R-Ig, or hp80 TNFR-Ig. All experiments were performed at 25C with a 10 ul/ml minute flow rate.

Each experiment was performed using HBS buffer (10MM HEPES, 150 mM NaCl, 0.005% P20 surfactant, at pH 7.4). The same solution was used both as running buffer and as sample diluent.

The CM5 chip (BIAcore, Inc.) surface was first activated with N-hydroxysuccinimide/N-ethyl-N'-(3-diethylamino-propyl)-carbodiimide hydrochloride (BIAcore). Twenty ul of hBCMA-Ig; fifteen ul of hLT-R05-Ig and 10 ul of hp80-TNFR, diluted to 30 g/ml in 10 mM acetic acid were then blocked with once with 30 ul and again with 15 ul of ethanolamine-HCL (pH 8.5). This resulted in a surface density of 1600-3700 resonance units (RU). The chip was regenerated with 20 ul of 1 mM formic acid. These rejections were repeated five times to establish a reproducible and stable baseline.

For the experiment, 100 ul of myc-mApril, hKayL-440, and FLAG-mBAFF each was diluted to 30 ug/ml in diluent buffers and was injected over the surface of the chip. Immediately after each injection, the chip was washed with 500 ul of the diluent buffer. The surface was regenerated between experiments by injecting 20 ul of 1 mM formic acid; followed with another 15 ul injection formic acid. After regeneration, the chip was equilibrated with the dilution buffer.

Example 4

Generation of Soluble Receptor Forms

To form a receptor inhibitor for use in humans, one requires the human receptor cDNA sequence of the extracellular domain. If the mouse form is known, human cDNA libraries can be easily screened using the mouse cDNA sequence and such manipulations are routinely carried out in this area. With a human cDNA sequence, one can design oligonucleotide primers to PCR amplify the extracellular domain of the receptor in the absence of the transmembrane and intracellular domains. Typically, one includes most of the amino acids between the last disulfide linked "TNF domain" and the transmembrane domain. One could vary the amount of "stalk" region included to optimize the potency of the resultant soluble receptor. This amplified piece would be engineered to include suitable restriction sites to allow cloning into various C-terminal Ig fusion chimera vectors. Alternatively, one could insert a stop signal at the 3' end and make a soluble form of the receptor without resorting to the use of a Ig fusion chimera approach. The resultant vectors can be expressed in most systems used in biotechnology including yeast, insect cells, bacteria and mammalian cells and examples exist for all types of expression. Various human Fc domains can be attached to optimize or eliminate FcR and complement interactions as desired. Alternatively, mutated forms of these Fc domains can be used to selectively remove FcR or complement interactions or the attachment of N-linked sugars to the Fc domain which has certain advantages.

Example 5

Generation of Agonistic or Antagonistic Antibodies

The above described soluble receptor forms can be used to immunize mice and to make monoclonal antibodies by conventional methods. The resultant mAbs that are identified by ELISA methods can be further screened for agonist activity either as soluble antibodies or immobilized on plastic in various in vitro cellular assays. Often the death of the HT29 cell line is a convenient system that is sensitive to signaling through many TNF receptors. If this line does not possess the receptor of interest, that full length receptor can be stably transfected into the HT29 line to now allow the cytotoxicity assay to work. Alternatively, such cells can be used in the Cytosensor apparatus to assess whether activation of the receptor can elicit a pH change that is indicative of a signaling event. TNF family receptors signal well in such a format and this method does not require one to know the actual biological events triggered by the receptor. The agonistic mAbs would be "humanized" for clinical use. This procedure can also be used to define antagonistic mAbs. Such mAbs would be defined by the lack of agonist activity and the ability to inhibit receptor-ligand interactions as monitored by ELISA, classical binding or BIAcore techniques. Lastly, the induction of chemokine secretion by various cells in response to an agonist antibody can form a screening assay.

Example 6

Screening for Inhibitors of the Receptor-Ligand Interaction

Using the receptor-Ig fusion protein, one can screen either combinatorial libraries for molecules that can bind the receptor directly. These molecules can then be tested in an ELISA formatted assay using the receptor-Ig fusion protein and a soluble form of the ligand for the ability to inhibit the receptor-ligand interaction. This ELISA can be used directly to screen various natural product libraries etc. for inhibitory compounds. The receptor can be transfected into a cell line such as the HT29 line to form a biological assay (in this case cytotoxicity) that can then form the screening assay.

Example 7

In vivo Tumor Growth Inhibition

The effectiveness of BCMA-Ig as a tumor growth antagonist was tested using a number of different tumor cell lines grown in vivo. Athymic (Nu/Nu), immunodeficient mice were used for these studies, and tumor cells were implanted subcutaneously. For the SW480 tumor line, which grows aggressively, we implanted $8 \times 10^5$ cells in 100 µl pyrogen-free, sterile PBS. One control group was left untreated (n=5), while other groups were dosed with 100 µgs control-Ig (n=6) or 100 µgs BCMA-Ig (n=6) proteins. Dosing began just prior to implantation, with subsequent doses every 7 days thereafter. Tumor diameter was measured using a micrometer, and the volume is calculated using the formula vol=$4/3 \Pi r^3$.

SW480 colon carcinoma tumors grow very quickly using the Nu/Nu mouse model, and palpable tumors were detected within 10 days. After 24 days the average control tumor volume was 0.3 $cm^3$, while the average volume of BCMA-Ig treated tumors was 0.19 $cm^3$, a reduction of 46% in tumor burden. The colon carcinoma HT29 also grows aggressively in the Nu/Nu model. For these experiments $1 \times 10^6$ cells in 100 µl pyrogen-free, sterile PBS were implanted subcutaneously, and the dosing regimen was as described for SW480. Palpable tumors were detected after 7 days, and in the control groups most of the tumors grew very rapidly. After 42 days the average tumor volume in the control groups (untreated and control-Ig treated, n=12) was 0.485 $cm^3$, while the average tumor size in the BCMA-Ig treated group (n=5) was 0.095 $cm^3$, a reduction of 80% in tumor burden. After 50 days 30% of the mice in the control group were scored as terminal due to tumor sizes greater than 1.5 $cm^3$, and the experiment was halted. In contrast to the control group 0% of the mice in the BCMA-Ig treated group were scored as terminal. These results are shown in table 2.

TABLE 2

Tumor volumes and lethality in the HT29 model after 50 days treatment.

| tumor vol | terminal |
|---|---|
| control animals (untreated and control-Ig treated) | |
| 0.22 | – |
| 0.22 | – |
| 0.35 | – |
| 0.61 | – |
| 0.73 | – |
| 1.74 | + |
| 2.53 | + |
| 1.51 | + |
| 0.90 | – |
| 0.44 | – |
| 0.32 | – |
| 1.92 | + |
| ave: 0.96 | %: 30 |
| BCMA-Ig treated | |
| 0.11 | – |
| 0.32 | – |
| 0.13 | – |
| 0.56 | – |
| 0.33 | – |
| ave: 0.29 | %: 0 |

This demonstrates a 70% reduction in average tumor volume and a significant effect on mortality in the HT29 model of tumor growth using BCMA-Ig treatment.

The lung carcinoma tumor line A549 grows more slowly than the colon carcinoma lines described above. For this cell line we implanted $1 \times 10^6$ cells in 100 µl pyrogen-free, sterile PBS, and treated using the regimen described previously. Palpable tumors were detected approximately 20 days after implantation. 50 days after tumor implantation the average tumor volume in the control groups (untreated and control-Ig treated; n=16) was 0.2 cm³ while the average tumor volume in the BCMA-Ig treated group (n=7) was 0.1 cm³, a reduction of 50% in tumor volume. In the BCMA-Ig treated group 57% of the mice had a tumor of less than 0.1 cm³ after 50 days, while only 6% of the control treated mice retained such a small tumor burden. 60 days after tumor implantation the average tumor volume in the control group had increased to 0.3 cm³. In contrast the average tumor volume in the BCMA-Ig treated group was still less than 0.2 cm³ (0.188).

For the murine NIH3T3 line, which also grows more slowly than the colon carcinoma lines, we implanted $5 \times 10^6$ cells in 100 µl pyrogen-free, sterile PBS, and treated as described above. The NIH3T3 cells form a fibrosarcoma tumor when implanted subcutaneously in Nu/Nu mice. After 4 weeks palpable tumors were detected, and in the control groups (n=11) these tumors expanded in volume over the next 10 days to reach an average size of 0.136 cm³. In contrast the tumor volume in the BCMA-Ig-treated group (n=5) only reached a size of 0.03 cm³, a 78% reduction in tumor burden. At day 48 after tumor implantation the average tumor volume in the controls groups had reached 1.6 cm³, while the average tumor volume in the BCMA-Ig treated group was only 0.8 cm³, a 50% reduction in tumor volume. By day 52, 82% (9/11) of the animals in the control groups had been scored as terminal based on a tumor volume of greater than 1.5 cm³, leaving only 18% of the animals still alive. In contrast 40% (2/5) of the animals in the BCMA-Ig treated group had a tumor of such volume that they had to be sacrificed, leaving 60% of the animals still alive. These results are tabulated in Table 3.

TABLE 3

Survivorship data in the NIH3T3 model.

| % survival | Days after implantation | | | |
|---|---|---|---|---|
| | 38 | 42 | 48 | 52 |
| control | 100 | 90 | 64 | 18 |
| BCMA-Ig | 100 | 100 | 80 | 60 |

The results showing the growth of NIH3T3 tumors over time are illustrated in FIG. 13. The results showing the growth of SW480 tumors over time are illustrated in FIG. 14. The results showing the growth of the HT29 tumors over time, and a scattergram showing individual animals on day 42 after tumor implantation, are illustrated in FIG. 15A. The results showing the growth of A549 tumors in individual animals on days 50 and 60 after tumor implantation are shown in FIG. 15B.

The results for the tumor growth inhibition for the NIH3T3 tumor cell line are shown in FIG. 13. The results for the tumor growth inhibition for the SW480 tumor cell line are shown in FIG. 14. The results for the tumor growth inhibition for the HT29 and A549 tumor cell lines are shown in FIG. 15.

Example 8

BCMA-IgG Causes a Reduction in the Number of B Cells in Normal Mice

Eight-week-old female BALB/c mice were purchased from The Jackson Laboratory (Bar Harbor, Me.).

Mice (3/group) received i.p. either PBS, 400 µg of human BCMA-huIgG1 (hBCMA-Ig) fusion protein (supplied by Teresa Cachero, Biogen), or 400 µg of purified human IgG (HuIgG) (Sandoz, Basel, Switzerland) on days −8, −5, −1 and +2. Mice received 100 µl of 10% sheep red blood cells (SRBC) (Colorado Serum Company, Denver, Colo.) on day 0.

At the time of sacrifice blood was collected via cardiac puncture into tubes containing EDT, and red blood cells were lysed in a hypotonic buffer. Blood was also collected without EDTA for serum preparation. Single cell suspensions were prepared from spleens and mesenteric lymph nodes (MLN) and red blood cells were lysed in a hypotonic buffer. Flow cytometry was performed using PE-conjugated anti-CD45R/B220, anti-syndecan/CD138 and anti-B7.2, and FITC-conjugated anti-IgM and anti-CD45R/B220. All mAbs were purchased from Pharmingen (San Diego, Calif.). Briefly, Fc receptors were blocked with 10 µg/ml Fc Block (Pharmingen) for 15 min. on ice, followed by addition of PE- and FITC-conjugated mabs and incubated on ice for 20-30 min. Cells were washed 1× and suspended in 0.5% paraformaldehyde. Cell fluorescence data were acquired on a FACSCalibur™ flow cytometer (Becton Dickinson, San Jose, Calif.) and analyzed using CELLQuest™ software (Becton Dickinson).

After treatment with hBCMA-Ig there was approximately a 50% reduction in the number of B cells in peripheral blood and in the peripheral lymphoid organs examined. $B220^{high}$ $IgM^{low}$ B cells accounted for 23.4% and 21.5% of cells in PBS-treated and HuIgG-treated mice, respectively, whereas this population represented only 9.9% of cells in hBCMA-Ig-treated mice. Plasma cells (sndecan/CD138+) appeared to be slightly decreased as well with 5.7% and 4.8% present in the blood of PBS-treated and HuIgG-treated mice, respectively, compared with 3.9% in hBCMA-Ig-treated mice. The B7.2 molecule was upregulated on 3.1% and 4.5% of B220+cells in PBS-treated and HuIgG-treated mice, respectively, compared with 1.9% in hBCMA-Ig-treated mice.

In the spleen $B220^{high}$ B cells were markedly reduced in hBCMA-Ig-treated mice representing 18.8%, compared with 36.7% and 40% in PBS- and HuIgG-treated mice, respectively. This decline was observed in both $IgM^{high}$ and $IgM^{low}$ subpopulations (see Table 1). There was no change observed in the newly formed B cell compartment in the spleen, $B220^{low}$ $IgM^{high}$ (data not shown). Plasma cells (syndecan/CD 138+) appeared to be slightly decreased as well with 3.3% and 3.4% present in the spleen of PBS-treated and HuIgG-treated mice, respectively, compared with 2.4% in hBCMA-Ig-treated mice.

The MLN exhibited a decline in B220+B cells with 14.1% present in hBCMA-Ig-treated mice compared with 26.7% and 35.8% in PBS-treated and HuIgG-treated mice, respectively. The data are summarized in Table 3.

TABLE 3

B cell populations in hBCMA-Ig, PBS and HuIgG-treated mice[1].

| Blood | B220$^{high}$ IgM$^{low}$ | Syndecan | B7.2/B220$^{low}$ |
|---|---|---|---|
| PBS | 23.4 ± 5.7 | 5.7 ± 1.5 | 3.1 ± 0.5 |
| HuIgG | 21.5 ± 4.5 | 4.8 ± 0.9 | 4.5 ± 1.0 |
| HBCMA-Ig | 9.9 ± 1.8 | 3.9 ± 0.6 | 1.9 ± 0.5 |

| Spleen | B220$^{high}$ IgM$^{low}$ | B220$^{high}$ IgM$^+$ | Syndecan |
|---|---|---|---|
| PBS | 27.8 ± 1.6 | 11.9 ± 1.6 | 3.3 ± 0.8 |
| HuIgG | 30.5 ± 2 | 11.8 ± 1.0 | 3.4 ± 0.7 |
| HBCMA-Ig | 10.6 ± 0.2 | 8.4 ± 0.2 | 2.4 ± 0.2 |

| MLN | B220$^+$ |
|---|---|
| PBS | 26.7 |
| HuIgG | 35.8 ± 3.3 |
| HBCMA-Ig | 14.1 ± 5.9 |

[1]The mice were treated as described in the Materials and Methods section, and the data are given as percent ± standard Deviation The decreased percentage of B7.2+B cells in the blood and plasma cells in the blood and spleens of hBCMA-Ig-treated mice after immunization with SRBCs suggests that there is inhibition of B cell activation and/or maturation, and potentially increased elimination of activated B cells. A very minor percent of antigen-specific B cells would be activated and respond to any antigen, in this case SRBC. Because the hBCMA-Ig treatment resulted in such a dramatic reduction in the percent of B cells in all tissues examined, ~50%, the activity of hBCMA-Ig appears to also target resting, mature B cells.

It is therefore contemplated that BCMA fusion protein may be used as a therapeutic drug with clinical application in B cell-mediated diseases. Diseases would include those that are autoimmune in nature such as systemic lupus erythematosus, myasthenia gravis, autoimmune hemolytic anemia, idiopathic thrombocytopenia purpura, anti-phospholipid syndrome, Chaga's disease, Grave's disease, Wegener's Granulomatosis, Poly-arteritis Nodosa and Rapidly Progressive Glomerulonephritis. The therapeutic agent would also have application in plasma cell disorders such as multiple myeloma, Waldenstrom's macroglobulinemia, Heavey-chain disease, Primary or immunocyte-associated amyloidosis, and Monoclonal gammopathy of undetermined significance (MGUS). Oncology targets would include B cell carcinomas, leukemias, and lymphomas.

It will be apparent to those skilled in the art that various modifications and variations can be made in the polypeptides, compositions and methods of the invention without departing from the spirit or scope of the invention. Thus, it is intended that the present invention cover the modifications and variations of this invention provided that they come within the scope of the appended claims and their equivalents.

SEQUENCE LISTING

<160> NUMBER OF SEQ ID NOS: 12

<210> SEQ ID NO 1
<211> LENGTH: 736
<212> TYPE: DNA
<213> ORGANISM: murine

<400> SEQUENCE: 1

```
ccaaacgatg agatttcctt caatttttac tgcagtttta ttcgcagcat cctccgcatt      60
agctgctcca gtcaacacta caacagaaga tgaaacggca caaattccgg ctgaagctgt     120
catcggttac tcagatttag aagggggattt cgatgttgct gttttgccat tttccaacag    180
cacaaataac gggttattgt ttataaatac tactattgcc agcattgctg ctaaagaaga    240 agggggtatct ctcgagaaaa gagaacaaaa actcatttct gaggaagatc tgaataaaga    300
gctccactca gtcctgcatc ttgttccagt taacattacc tccaaggact ctgacgtgac    360
agaggtgatg tggcaaccag tacttaggcg tgggagaggc ctggaggccc agggagacat    420
tgtacgagtc tgggacactg gaatttatct gctctatagt caggtcctgt ttcatgatgt    480
gactttcaca atgggtcagg tggtatctcg ggaaggacaa gggagaagag aaactctatt    540
ccgatgtatc agaagtatgc cttctgatcc tgaccgtgcc tacaatagct gctacagtgc   600
aggtgtcttt catttacatc aagggggatat tatcactgtc aaaattccac gggcaaacgc    660
aaaacttagc ctttctccgc atggaacatt cctgggggttt gtgaaactat gagcggccgc   720
gaattaattc gcctta                                                    736
```

<210> SEQ ID NO 2
<211> LENGTH: 736

<212> TYPE: DNA
<213> ORGANISM: murine

<400> SEQUENCE: 2

```
ggtttgctac tctaaaggaa gttaaaaatg acgtcaaaat aagcgtcgta ggaggcgtaa      60
tcgacgaggt cagttgtgat gttgtcttct actttgccgt gtttaaggcc gacttcgaca     120
gtagccaatg agtctaaatc ttcccctaaa gctacaacga caaaacggta aaaggttgtc     180
gtgtttattg cccaataaca aatatttatg atgataacgg tcgtaacgac gatttcttct     240
tccccataga gagctctttt ctcttgtttt tgagtaaaga ctccttctag acttatttct     300
cgaggtgagt caggacgtag aacaaggtca attgtaatgg aggttcctga gactgcactg     360
tctccactac accgttggtc atgaatccgc accctctccg gacctccggg tccctctgta     420
acatgctcag accctgtgac cttaaataga cgagatatca gtccaggaca aagtactaca     480
ctgaaagtgt tacccagtcc accatagagc ccttcctgtt ccctcttctc tttgagataa     540
ggctacatag tcttcatacg gaagactagg actggcacga atgttatcga cgatgtcacg     600
tccacagaaa gtaaatgtag ttcccctata atagtgacag ttttaaggtg cccgtttgcg     660
ttttgaatcg gaaagaggcg taccttgtaa ggaccccaaa cactttgata ctcgccggcg     720
cttaattaag cggaat                                                     736
```

<210> SEQ ID NO 3
<211> LENGTH: 234
<212> TYPE: PRT
<213> ORGANISM: homo sapiens

<400> SEQUENCE: 3

```
Met Arg Phe Pro Ser Ile Phe Thr Ala Val Leu Phe Ala Ala Ser Ser
  1               5                  10                  15

Ala Leu Ala Ala Pro Val Asn Thr Thr Thr Glu Asp Glu Thr Ala Gln
                 20                  25                  30

Ile Pro Ala Glu Ala Val Ile Gly Tyr Ser Asp Leu Glu Gly Asp Phe
             35                  40                  45

Asp Val Ala Val Leu Pro Phe Ser Asn Ser Thr Asn Asn Gly Leu Leu
         50                  55                  60

Phe Ile Asn Thr Thr Ile Ala Ser Ile Ala Ala Lys Glu Glu Gly Val
 65                  70                  75                  80

Ser Leu Glu Lys Arg Glu Gln Lys Leu Ile Ser Glu Glu Asp Leu Asn
                 85                  90                  95

Lys Glu Leu His Ser Val Leu His Leu Val Pro Val Asn Ile Thr Ser
                100                 105                 110

Lys Asp Ser Asp Val Thr Glu Val Met Trp Gln Pro Val Leu Arg Arg
            115                 120                 125

Gly Arg Gly Leu Glu Ala Gln Gly Asp Ile Val Arg Val Trp Asp Thr
        130                 135                 140

Gly Ile Tyr Leu Leu Tyr Ser Gln Val Leu Phe His Asp Val Thr Phe
145                 150                 155                 160

Thr Met Gly Gln Val Val Ser Arg Glu Gly Gln Gly Arg Arg Glu Thr
                165                 170                 175

Leu Phe Arg Cys Ile Arg Ser Met Pro Ser Asp Pro Asp Arg Ala Tyr
            180                 185                 190

Asn Ser Cys Tyr Ser Ala Gly Val Phe His Leu His Gln Gly Asp Ile
        195                 200                 205

Ile Thr Val Lys Ile Pro Arg Ala Asn Ala Lys Leu Ser Leu Ser Pro
```

```
                210              215              220
His Gly Thr Phe Leu Gly Phe Val Lys Leu
225             230

<210> SEQ ID NO 4
<211> LENGTH: 542
<212> TYPE: DNA
<213> ORGANISM: homo sapiens

<400> SEQUENCE: 4
ttaatcaaaa catggctatc atctacctca tcctcctgtt caccgctgtg cggggcgatt    60
acaaagacga tgacgataaa ggacccggac aggtgcagct gcagaaacag aagaagcagc   120
actctgtcct gcacctggtt cccattaacg ccacctccaa ggatgactcc gatgtgacag   180
aggtgatgtg gcaaccagct cttaggcgtg ggagaggcct acaggcccaa ggatatggtg   240
tccgaatcca ggatgctgga gtttatctgc tgtatagcca ggtcctgttt caagacgtga   300 cttttcaccat gggtcaggtg gtgtctcgag aaggccaagg aaggcaggag actctattcc   360
gatgtataag aagtatgccc tcccacccgg accgggccta caacagctgc tatagcgcag   420
gtgtcttcca tttacaccaa ggggatattc tgagtgtcat aattccccgg gcaagggcga   480
aacttaacct ctctccacat ggaaccttcc tggggtttgt gaaactgtga tctagagggc   540
cc                                                                  542

<210> SEQ ID NO 5
<211> LENGTH: 542
<212> TYPE: DNA
<213> ORGANISM: homo sapiens

<400> SEQUENCE: 5
aattagtttt gtaccgatag tagatggagt aggaggacaa gtggcgacac gccccgctaa    60
tgtttctgct actgctattt cctgggcctg tccacgtcga cgtctttgtc ttcttcgtcg   120
tgagacagga cgtggaccaa gggtaattgc ggtggaggtt cctactgagg ctacactgtc   180
tccactacac cgttggtcga gaatccgcac cctctccgga tgtccgggtt cctataccac   240
aggcttaggt cctacgacct caaatagacg acatatcggt ccaggacaaa gttctgcact   300
gaaagtggta cccagtccac cacagagctc ttccggttcc ttccgtcctc tgagataagg   360
ctacatattc ttcatacggg agggtgggcc tggcccggat gttgtcgacg atatcgcgtc   420
cacagaaggt aaatgtggtt cccctataag actcacagta ttaagggggcc cgttcccgct   480 ttgaattgga gagaggtgta ccttggaagg accccaaaca ctttgacact agatctcccg   540
gg                                                                  542

<210> SEQ ID NO 6
<211> LENGTH: 172
<212> TYPE: PRT
<213> ORGANISM: homo sapiens

<400> SEQUENCE: 6

Met Ala Ile Ile Tyr Leu Ile Leu Leu Phe Thr Ala Val Arg Gly Asp
 1               5                  10                  15

Tyr Lys Asp Asp Asp Asp Lys Gly Pro Gly Gln Val Gln Leu Gln Lys
                20                  25                  30

Gln Lys Lys Gln His Ser Val Leu His Leu Val Pro Ile Asn Ala Thr
            35                  40                  45

Ser Lys Asp Asp Ser Asp Val Thr Glu Val Met Trp Gln Pro Ala Leu
```

```
                  50                  55                  60
Arg Arg Gly Arg Gly Leu Gln Ala Gln Gly Tyr Gly Val Arg Ile Gln
 65                  70                  75                  80

Asp Ala Gly Val Tyr Leu Leu Tyr Ser Gln Val Leu Phe Gln Asp Val
                 85                  90                  95

Thr Phe Thr Met Gly Gln Val Val Ser Arg Glu Gly Gln Gly Arg Gln
                100                 105                 110

Glu Thr Leu Phe Arg Cys Ile Arg Ser Met Pro Ser His Pro Asp Arg
                115                 120                 125

Ala Tyr Asn Ser Cys Tyr Ser Ala Gly Val Phe His Leu His Gln Gly
            130                 135                 140

Asp Ile Leu Ser Val Ile Pro Arg Ala Arg Ala Lys Leu Asn Leu
145                 150                 155                 160

Ser Pro His Gly Thr Phe Leu Gly Phe Val Lys Leu
                165                 170

<210> SEQ ID NO 7
<211> LENGTH: 555
<212> TYPE: DNA
<213> ORGANISM: homo sapiens

<400> SEQUENCE: 7
atgttgcaga tggctgggca gtgctcccaa atgaatatt  ttgacagttt gttgcatgct     60
tgcataccct tgtcaacttcg atgttcttct aatactcctc ctctaacatg tcagcgttat    120
tgtaatgcaa gtgtgaccaa ttcagtgaaa ggaacgaatg cgattctctg gacctgtttg    180
ggactgagct taataatttc tttggcagtt ttcgtgctaa tgttttttgct aaggaagata   240 agctctgaac cattaaagga cgagtttaaa aacacaggat caggtctcct gggcatggct    300
aacattgacc tggaaaagag caggactggt gatgaaatta ttcttccgag aggcctcgag    360
tacacggtgg aagaatgcac ctgtgaagac tgcatcaaga gcaaaccgaa ggtcgactct    420
gaccattgct ttccactccc agctatggag gaaggcgcaa ccattcttgt caccacgaaa    480
acgaatgact attgcaagag cctgccagct gctttgagtg ctacggagat agagaaatca    540
atttctgcta ggtaa                                                     555

<210> SEQ ID NO 8
<211> LENGTH: 184
<212> TYPE: PRT
<213> ORGANISM: homo sapiens

<400> SEQUENCE: 8

Met Leu Gln Met Ala Gly Gln Cys Ser Gln Asn Glu Tyr Phe Asp Ser
 1               5                  10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
         50                  55                  60

Ile Ile Ser Leu Ala Val Phe Val Leu Met Phe Leu Leu Arg Lys Ile
 65                  70                  75                  80

Ser Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
                100                 105                 110
```

```
Ile Ile Leu Pro Arg Gly Leu Glu Tyr Thr Val Glu Glu Cys Thr Cys
            115                 120                 125

Glu Asp Cys Ile Lys Ser Lys Pro Lys Val Asp Ser Asp His Cys Phe
130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180
```

```
<210> SEQ ID NO 9
<211> LENGTH: 483
<212> TYPE: DNA
<213> ORGANISM: homo sapiens

<400> SEQUENCE: 9
gttgaagcta caagaagatt atgaggagga gattgtacag tcgcaataac attacgttca      60
cactggttaa gtcactttcc ttgcttacgc taagagacct ggacaaaccc tgactcgaat     120
tattaaagaa accgtcaaaa gcacgattac aaaaacgatt ccttctattc gagacttggt     180
aatttcctgc tcaaattttt gtgtcctagt ccagaggacc cgtaccgatt gtaactggac     240
cttttctcgt cctgaccact actttaataa aaggctctc cggagctcat gtgccacctt      300
cttacgtgga cacttctgac gtagttctcg tttggcttcc agctgagact ggtaacgaaa     360
ggtgagggtc gataccctcct tccgcgttgg taagaacagt ggtgcttttg cttactgata    420
acgttctcgg acggtcgacg aaactcacga tgcctctatc tctttagtta aagacgatcc     480
att                                                                   483

<210> SEQ ID NO 10
<211> LENGTH: 483
<212> TYPE: DNA
<213> ORGANISM: homo sapiens

<400> SEQUENCE: 10
caacttcgat gttcttctaa tactcctcct ctaacatgtc agcgttattg taatgcaagt      60
gtgaccaatt cagtgaaagg aacgaatgcg attctctgga cctgtttggg actgagctta     120
ataatttctt tggcagtttt cgtgctaatg ttttttgctaa ggaagataag ctctgaacca    180
ttaaaggacg agtttaaaaa cacaggatca ggtctcctgg gcatggctaa cattgacctg    240
gaaaagagca ggactggtga tgaaattatt cttccgagag gcctcgagta cacggtggaa     300
gaatgcacct gtgaagactg catcaagagc aaaccgaagg tcgactctga ccattgcttt    360
ccactcccag ctatggagga aggcgcaacc attcttgtca ccacgaaaac gaatgactat    420
tgcaagagcc tgccagctgc tttgagtgct acggagatag agaaatcaat ttctgctagg    480
taa                                                                   483

<210> SEQ ID NO 11
<211> LENGTH: 906
<212> TYPE: DNA
<213> ORGANISM: homo sapiens

<400> SEQUENCE: 11
atggagacag acacactcct gttatgggtg ctgctgctct ggttccaggt tccactggt      60 gacgtcacga tgttgcagat ggctgggcag tgctcccaaa atgaatattt tgacagtttg    120
```

```
ttgcatgctt gcataccttg tcaacttcga tgttcttcta atactcctcc tctaacatgt      180
cagcgttatt gtaatgcaag tgtgaccaat tcagtgaaag gagtcgacaa aactcacaca      240
tgcccaccgt gcccagcacc tgaactcctg gggggaccgt cagtcttcct cttcccccca      300
aaacccaagg acaccctcat gatctcccgg acccctgagg tcacatgcgt ggtggtggac      360
gtgagccacg aagaccctga ggtcaagttc aactggtacg tggacggcgt ggaggtgcat      420
aatgccaaga caaagccgcg ggaggagcag tacaacagca cgtaccgtgt ggtcagcgtc      480
ctcaccgtcc tgcaccagga ctggctgaat ggcaaggagt acaagtgcaa ggtctccaac      540
aaagccctcc cagcccccat cgagaaaacc atctccaaag ccaagggca gccccgagaa       600 ccacaggtgt acaccctgcc cccatcccgg gatgagctga ccaagaacca ggtcagcctg      660
acctgcctgg tcaaaggctt ctatcccagc gacatcgccg tggagtggga gagcaatggg      720
cagccggaga acaactacaa gaccacgcct cccgtgttgg actccgacgg ctccttcttc      780
ctctacagca agctcaccgt ggacaagagc aggtggcagc aggggaacgt cttctcatgc      840
tccgtgatgc atgaggctct gcacaaccac tacacgcaga gagcctctc cctgtctccc       900 gggaaa                                                                  906
```

<210> SEQ ID NO 12
<211> LENGTH: 302
<212> TYPE: PRT
<213> ORGANISM: homo sapiens

<400> SEQUENCE: 12

```
Met Glu Thr Asp Thr Leu Leu Leu Trp Val Leu Leu Leu Trp Val Pro
  1               5                  10                  15

Gly Ser Thr Gly Asp Val Thr Met Leu Gln Met Ala Gly Gln Cys Ser
                 20                  25                  30

Gln Asn Glu Tyr Phe Asp Ser Leu Leu His Ala Cys Ile Pro Cys Gln
             35                  40                  45

Leu Arg Cys Ser Ser Asn Thr Pro Pro Leu Thr Cys Gln Arg Tyr Cys
         50                  55                  60

Asn Ala Ser Val Thr Asn Ser Val Lys Gly Val Asp Lys Thr His Thr
 65                  70                  75                  80

Cys Pro Pro Cys Pro Ala Pro Glu Leu Leu Gly Gly Pro Ser Val Phe
                 85                  90                  95

Leu Phe Pro Pro Lys Pro Lys Asp Thr Leu Met Ile Ser Arg Thr Pro
            100                 105                 110

Glu Val Thr Cys Val Val Val Asp Val Ser His Glu Asp Pro Glu Val
        115                 120                 125

Lys Phe Asn Trp Tyr Val Asp Gly Val Glu Val His Asn Ala Lys Thr
    130                 135                 140

Lys Pro Arg Glu Glu Gln Tyr Asn Ser Thr Tyr Arg Val Val Ser Val
145                 150                 155                 160

Leu Thr Val Leu His Gln Asp Trp Leu Asn Gly Lys Glu Tyr Lys Cys
                165                 170                 175

Lys Val Ser Asn Lys Ala Leu Pro Ala Pro Ile Glu Lys Thr Ile Ser
            180                 185                 190

Lys Ala Lys Gly Gln Pro Arg Glu Pro Gln Val Tyr Thr Leu Pro Pro
        195                 200                 205

Ser Arg Asp Glu Leu Thr Lys Asn Gln Val Ser Leu Thr Cys Leu Val
    210                 215                 220
```

```
                                          -continued
Lys Gly Phe Tyr Pro Ser Asp Ile Ala Val Glu Trp Glu Ser Asn Gly
225                 230                 235                 240

Gln Pro Glu Asn Asn Tyr Lys Thr Thr Pro Pro Val Leu Asp Ser Asp
                245                 250                 255

Gly Ser Phe Phe Leu Tyr Ser Lys Leu Thr Val Asp Lys Ser Arg Trp
            260                 265                 270

Gln Gln Gly Asn Val Phe Ser Cys Ser Val Met His Glu Ala Leu His
        275                 280                 285

Asn His Tyr Thr Gln Lys Ser Leu Ser Leu Ser Pro Gly Lys
    290                 295                 300
```

What is claimed is:

1. A method of treating a mammal for a tumor that expresses A Proliferation Inducing Ligand (APRIL), said method comprising administering to the mammal a therapeutically effective amount of a polypeptide capable of binding to APRIL, wherein the polypeptide comprises at least one of the following amino acid sequences:
   (a) an amino acid sequence which is at least 95% identical to amino acids 8 to 41 of SEQ ID NO:8; and
   (b) an amino acid sequence which is at least 95% identical to amino acids 1 to 52 of SEQ ID NO:8.

2. The method of claim 1, wherein the polypeptide comprises amino acids 8 to 41 of SEQ ID NO:8.

3. The method of claim 1, wherein the polypeptide further comprises a signal sequence of a secreted protein.

4. The method of claim 1, wherein the polypeptide further comprises an Fc domain of an immunoglobulin.

5. The method of claim 4, wherein the immunoglobulin is IgG.

6. The method of claim 5, wherein the immunoglobulin is human.

7. The method of claim 6, wherein the polypeptide comprises amino acids 24-302 of SEQ ID NO:12.

8. The method of any one of claims 1-7, wherein the mammal is a human.

9. The method of any one of claims 1-7, wherein the tumor is a carcinoma.

10. The method of claim 9, wherein the mammal is a human.

11. The method of claim 9, wherein the carcinoma is selected from the group consisting of lung carcinoma, colon carcinoma, prostate carcinoma, and breast carcinoma.

12. The method of claim 11, wherein the mammal is a human.

13. A method of inhibiting the activity of A Proliferation Inducing Ligand (APRIL) in a mammal having a tumor that expresses APRIL, said method comprising administering to the mammal an effective amount of a polypeptide capable of binding to APRIL, wherein the polypeptide comprises at least one of the following amino acid sequences:
   (a) an amino acid sequence which is at least 95% identical to amino acids 8 to 41 of SEQ ID NO:8; and
   (b) an amino acid sequence which is at least 95% identical to amino acids 1 to 52 of SEQ ID NO:8.

14. The method of claim 13, wherein the polypeptide comprises amino acids 8 to 41 of SEQ ID NO:8.

15. The method of claim 13, wherein the polypeptide further comprises a signal sequence of a secreted protein.

16. The method of claim 13, wherein the polypeptide further comprises an Fc domain of an immunoglobulin.

17. The method of claim 16, wherein the immunoglobulin is IgG.

18. The method of claim 17, wherein the immunoglobulin is human.

19. The method of claim 18, wherein the polypeptide comprises amino acids 24-302 of SEQ ID NO:12.

20. The method of any one of claims 13-19, wherein the mammal is a human.

21. The method of any one of claims 13-19, wherein the tumor is a carcinoma.

22. The method of claim 21, wherein the mammal is a human.

23. The method of claim 21, wherein the carcinoma is selected from the group consisting of lung carcinoma, colon carcinoma, prostate carcinoma, and breast carcinoma.

24. The method of claim 23, wherein the mammal is a human.

* * * * *